(12) United States Patent
Burgaud et al.

(10) Patent No.: US 7,399,320 B2
(45) Date of Patent: Jul. 15, 2008

(54) USE OF TETRA-AZAPENTAMETHINE COMPOUNDS AS DIRECT DYEING AGENTS AND NOVEL TETRA-AZAPENTAMETHINE COMPOUNDS

(75) Inventors: Herve Burgaud, Damartin en Goele (FR); Herve David, Joinville le Pont (FR); Rui Pereira, Bussy St. Georges (FR); Beatrice Belcour-Castro, Joinville le Pont (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 12/000,223

(22) Filed: Dec. 11, 2007

(65) Prior Publication Data

US 2008/0092307 A1 Apr. 24, 2008

Related U.S. Application Data

(63) Continuation of application No. 10/489,855, filed as application No. PCT/FR03/02090 on Jul. 4, 2003, now Pat. No. 7,311,736.

(30) Foreign Application Priority Data

Jul. 5, 2002 (FR) .................................. 02 08494

(51) Int. Cl.
*A61Q 5/10* (2006.01)
*C07D 233/00* (2006.01)
*C07D 211/00* (2006.01)

(52) U.S. Cl. ...................... 8/405; 8/407; 8/437; 8/451; 8/463; 8/466; 8/570; 8/571; 8/572; 8/573; 8/574; 548/318.1; 548/321.1; 548/400; 546/184

(58) Field of Classification Search ............... 8/405, 8/407, 437, 451, 463, 466, 570, 571, 572, 8/573, 574; 548/318.1, 321.1, 400; 546/184
See application file for complete search history.

(56) References Cited

U.S. PATENT DOCUMENTS 6,884,266 B2 * 4/2005 Vidal et al. ................... 8/405

FOREIGN PATENT DOCUMENTS

WO    WO 02/078657 A1 * 10/2002

* cited by examiner

*Primary Examiner*—Eisa B Elhilo
(74) *Attorney, Agent, or Firm*—Oblon, Spivak, McClelland, Maier & Neustadt, P.C.

(57) ABSTRACT

The invention concerns the use as direct dyeing agent of at least one tetra-azapentamethine compound, a dyeing composition comprising at least such a compound, as well as a method for dyeing keratinous fibers, in particular human keratinous fibers and more particularly hair, which consists in applying at least one composition comprising such a compound. The composition also concerns tetra-azapentamethine compounds of formula (I). The invention further concerns a method for bleaching such compounds, as well as bleaching keratinous fibers previously dyed therewith.

29 Claims, No Drawings

USE OF TETRA-AZAPENTAMETHINE COMPOUNDS AS DIRECT DYEING AGENTS AND NOVEL TETRA-AZAPENTAMETHINE COMPOUNDS

CROSS-REFERENCE TO RELATED APPLICATIONS

This application is a continuation of the U.S. application Ser. No. 10/489,855, filed Sep. 24, 2004 now a U.S. Pat. No. 7,311,736 B2, which is a 371 of PCT/FR03/02090 filed on Jul. 4, 2003 and claims priority of FRANCE Application 02/08494 filed on Jul. 5, 2002.

FIELD OF THE INVENTION

The present invention relates to the field of dyeing keratin fibers, and relates more particularly to the use, as a direct dye, of at least one tetraazepentamethine compound, to a dye composition comprising at least one such compound and to a process for dyeing keratin fibers in which at least one composition comprising such a compound is applied.

The present invention also relates to novel tetraazapentamethine compounds and to the process for preparing them.

BACKGROUND OF THE INVENTION

It is known practice to dye keratin fibers, and in particular human hair, with dye compositions containing oxidation dye precursors, which are generally known as oxidation bases, such as ortho- or para-phenylenediamines, ortho- or para-aminophenols and heterocyclic compounds. These oxidation bases are colorless or weakly colored compounds, which, when combined with oxidizing products, give rise to colored compounds via a process of oxidative condensation.

It is also known that the shades obtained with these oxidation bases can be varied by combining them with couplers or coloration modifiers, the latter agents being chosen especially from aromatic meta-diamines, meta-aminophenols, meta-diphenols and certain heterocyclic compounds such as indole compounds.

The variety of molecules used as oxidation bases and couplers allows a wide range of colors to be obtained.

This oxidation dyeing process consists in applying to keratin fibers oxidation bases or a mixture of oxidation bases and couplers with an oxidizing agent, for example aqueous hydrogen peroxide solution, leaving the mixture to act and then rinsing the fibers. The colorations resulting therefrom are permanent, strong and resistant to external agents, especially light, bad weather, washing, perspiration and rubbing. This process, which is generally performed at basic pH, makes it possible simultaneously to obtain dyeing and lightening of the fiber, which is reflected in practice by the possibility of obtaining a final coloration that is lighter than the original color. In addition, the lightening of the fiber has the advantageous effect of giving rise to a unified color in the case of gray hair, and of bringing out the color, i.e. of making it more visible, in the case of naturally pigmented hair.

It is also known practice to dye keratin fibers by direct dyeing. The process conventionally used in direct dyeing consists in applying to keratin fibers direct dyes, which are colored and coloring molecules that have affinity for the fibers, leaving the dyes to act and then rinsing the fibers.

It is known practice, for example, to use nitrobenzene, anthraquinone, nitropyridine, azo, xanthene, acridine, azine or triarylmethane direct dyes.

This results in colorations that are particularly chromatic, but are, however, temporary or semipermanent on account of the nature of the bonds between the direct dyes and the keratin fiber. These interactions are such that the dyes are easily desorbed from the surface and/or from the core of the fiber. The colorations generally show low dyeing power and poor fastness with respect to washing or perspiration. These direct dyes are also generally light-sensitive, since the resistance of the chromophore with respect to photochemical attack is low, which leads to fading of the coloration of the hair over time. In addition, the sensitivity of these dyes to light depends on their uniform distribution or their distribution as aggregates in and/or on the keratin fiber.

It is known practice to use direct dyes in combination with oxidizing agents. However, the direct dyes are generally sensitive to the action of oxidizing agents such as aqueous hydrogen peroxide solution, which generally makes them difficult to use in lightening direct dye compositions based on aqueous hydrogen peroxide solution and on a basifying agent, or in oxidation dye compositions based on oxidation dyes.

Thus, it was proposed in patent applications FR-1 584 965 and JP-062 711 435 to dye the hair with dye compositions based on nitro direct dyes and/or on azo dispersed dyes and ammoniacal hydrogen peroxide solution, by applying to the hair a mixture of said dyes and of said oxidizing agent, prepared just before use. However, the colorations obtained are found to be insufficiently fast and disappear on shampooing, leaving the lightening of the hair fiber to show through. Such a coloration becomes unattractive by changing over time.

It has also been proposed in patent applications JP-53 95693 and JP-55 022638 to dye the hair with compositions based on cationic direct dyes of oxazine type and ammoniacal hydrogen peroxide solution, by applying to the hair, in first step, ammoniacal hydrogen peroxide solution, and then, in a second step, a composition based on the oxazine direct dye. This coloration is unsatisfactory, due to the fact that it requires a process that is made too slow by the leave-in times of the two successive steps. If, moreover, an extemporaneous mixture of the oxazine direct dye with ammoniacal hydrogen peroxide solution is applied to the hair, no coloration, or at the very most a virtually nonexistent coloration, of the hair fiber is obtained.

More recently, patent application FR 2 741 798 has described dye compositions containing azo or azomethine direct dyes comprising at least one quaternized nitrogen atom, said compositions needing to be mixed extemporaneously at basic pH with an oxidizing composition. These compositions allow fast, shiny colorations with uniform glints to be obtained. However, they do not allow keratin fibers to be dyed as strongly as with oxidation dye compositions.

Moreover, patent application FR 1 353 497, which does not however concern the dyeing of keratin fibers, discloses tetraazapentamethine compounds substituted with a benzimidazole radical and with a benzimidazolium group, which are particularly suitable for dyeing fibers based on acrylic nitrile polymers or copolymers.

There is thus a real need for direct dyes that do not have the drawbacks of those of the prior art.

DETAILED DESCRIPTION OF THE INVENTION

The Applicant has discovered, advantageously and unexpectedly, that it is possible to achieve this aim by using at least one monocationic tetraazapentamethine compound of formula (I).

These direct dyes are chromatic and allow keratin fibers to be dyed as strongly as with oxidation dyes, they are just as light-stable as oxidation dyes, and they are also resistant to bad weather, washing and perspiration. These direct dyes allow keratin fibers to be dyed in a very wide and in particular very chromatic range of colors, without forgetting the "fundamental" shades such as blacks and browns.

One subject of the present patent application is thus the use, as a direct dye in or for the manufacture of dye compositions for keratin fibers, in particular for human keratin fibers and more particularly the hair, of at least one tetraazapentamethine compound of formula (I)

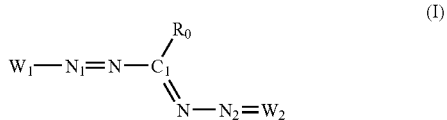

(I)

in which
$W_1$ represents a cationic heteroaromatic radical of formula (II) or (III):

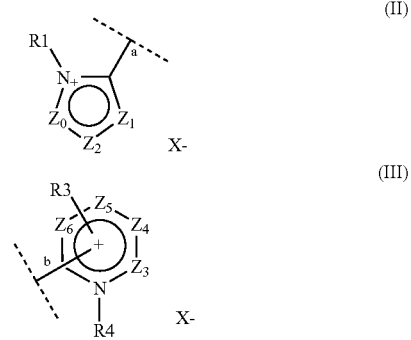

$W_2$ represents a heteroaromatic radical of formula (IV) or (V):

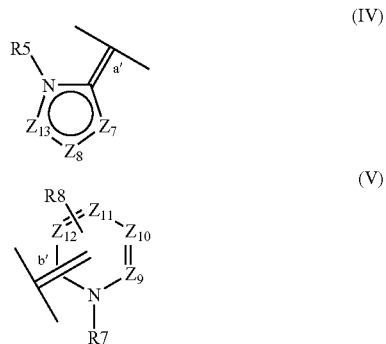

in which:
$Z_0$ represents a radical $CR_2$, a nitrogen atom or a radical $NR_{21}$,
$Z_1$ represents an oxygen or sulfur atom or a radical $NR_9$,
$Z_2$ represents a nitrogen atom or a radical $CR_{10}$,
$Z_3$ represents a nitrogen atom or a radical $CR_{11}$,
$Z_4$ represents a nitrogen atom or a radical $CR_{12}$,
$Z_5$ represents a nitrogen atom or a radical $CR_{13}$,
$Z_6$ represents a nitrogen atom or a radical $CR_{14}$,
$Z_7$ represents an oxygen or sulfur atom or a radical $NR_{15}$,
$Z_8$ represents a nitrogen atom or a radical $CR_{16}$,
$Z_9$ represents a nitrogen atom or a radical $CR_{17}$,
$Z_{10}$ represents a nitrogen atom or a radical $CR_{18}$,
$Z_{11}$ represents a nitrogen atom or a radical $CR_{19}$,
$Z_{12}$ represents a nitrogen atom or a radical $CR_{20}$,
$Z_{13}$ represents a radical $CR_6$, a nitrogen atom or a radical $NR_{22}$,
it being understood that each of the rings of formulae (II), (III), (IV) and (V) comprise not more than three nitrogen atoms and that two of the three nitrogen atoms may be contiguous,
the bond a of the 5-membered cationic heteroaromatic radical of formula (II) being linked to the nitrogen atom $N_1$ of formula (I),
the bond b of the 6-membered cationic heteroaromatic radical of formula (III) being linked to the nitrogen atom $N_1$ of formula (I),
the double bond a' of the 5-membered heteroaromatic radical of formula (IV) being linked to the nitrogen atom $N_2$ of formula (I),
the double bond b' of the 6-membered heteroaromatic radical of formula (V) being linked to the nitrogen atom $N_2$ of formula (I),
the bond b, linking the cationic heteroaromatic radical of formula (III) to the nitrogen atom $N_1$ of formula (I), being in an ortho or para position relative to the nitrogen atom bearing the radical $R_4$ when $Z_5$ represents a radical $CR_{13}$; the bond b being in an ortho position relative to the nitrogen atom bearing the radical $R_4$ when $Z_5$ represents a nitrogen atom,
the bond b', linking the heteroaromatic radical of formula (V) to the nitrogen atom $N_2$ of formula (I), being in an ortho or para position relative to the nitrogen atom bearing the radical $R_7$ when $Z_{11}$ represents a radical $CR_{19}$; the bond b' being in an ortho position relative to the nitrogen atom bearing the radical $R_7$ when $Z_{11}$ represents a nitrogen atom,
$R_2$, $R_6$, $R_{10}$ and $R_{16}$ represent, independently of each other, a hydrogen atom; a linear or branched $C_1$-$C_4$ alkyl radical, which is unsubstituted or substituted with one to three radicals chosen from hydroxyl, $C_1$-$C_2$ alkoxy, $C_2$-$C_4$ (poly)hydroxyalkoxy, amino, $C_1$-$C_2$ (di)alkylamino, carboxyl and sulfonic radicals; a phenyl radical, which is unsubstituted or substituted with one or two radicals chosen from hydroxyl, $C_1$-$C_2$ alkoxy, $C_2$-$C_4$ (poly)hydroxyalkoxy, amino and $C_1$-$C_2$ (di)alkylamino radicals; a carboxyl radical; a sulfonylamino radical,
$R_1$, $R_4$, $R_5$, $R_7$, $R_9$, $R_{15}$, $R_{21}$ and $R_{22}$ represent, independently of each other, a linear or branched $C_1$-$C_8$ alkyl radical, which is unsubstituted or substituted with one to three radicals chosen from hydroxyl, $C_1$-$C_2$ alkoxy, $C_2$-$C_4$ (poly)hydroxyalkoxy, amino, $C_1$-$C_2$ (di)alkylamino, carboxyl and sulfonic radicals;
$R_0$ $R_3$, $R_8$, $R_{11}$, $R_{12}$, $R_{13}$, $R_{14}$, $R_{17}$, $R_{18}$, $R_{19}$ and $R_{20}$ represent, independently of each other, a hydrogen atom, a linear or branched $C_1$-$C_{16}$ hydrocarbon-based chain, this chain possibly being saturated or unsaturated with one to three unsaturations, this chain being unsubstituted or substituted with one to three radicals chosen from hydroxyl, $C_1$-$C_2$ alkoxy, $C_2$-$C_4$ (poly)hydroxyalkoxy, amino, $C_1$-$C_2$ (di)alkylamino, carboxyl, sulfonic, sulfonylamino and $C_2$-$C_4$ (poly)hydroxyalkylamino radicals or a halogen atom such as chlorine, fluorine or bromine; a phenyl radical, which is unsubstituted or substituted with one to three radicals chosen from hydroxyl, $C_1$-$C_2$ alkoxy, $C_2$-$C_4$ (poly)hydroxyalkoxy, amino, $C_1$-$C_2$ (di)alkylamino, carboxyl, sulfonic, sulfonylamino and $C_2$-$C_4$ (poly)hydroxyalkylamino radicals or a halogen atom such as chlorine, fluorine or bromine; a heteroaryl radical chosen from pyrazolyl, pyrrolyl, imidazolyl, thiazolyl, oxazolyl, triazolyl, pyridyl, pyrimidinyl, triazinyl, pyrazinyl and pyridazinyl radicals; in addition, this hydrocarbon-based chain may be interrupted with one or two oxygen, nitrogen or sulfur atoms or with an $SO_2$ radical, it being understood that $R_0$, $R_3$, $R_8$, $R_{11}$, $R_{12}$, $R_{13}$, $R_{14}$, $R_{17}$, $R_{18}$, $R_{19}$ and $R_{20}$ do not comprise a peroxide bond or diazo or nitroso radicals, $R_2$ with $R_{10}$, $R_{11}$ with $R_{12}$, $R_6$ with $R_{16}$, and $R_{17}$ with $R_{18}$ can form, independently of each other, a 5- or 6-membered carbon-based aromatic ring, which is unsubstituted or substituted with one or two hydroxyl, amino, (di) ($C_1$-$C_2$)alkylamino, $C_1$-$C_2$ alkoxy or $C_2$-$C_4$ (poly)hydroxyalkylamino radicals, X is an organic or mineral anion.

For the purposes of the present patent application, the expression "branched hydrocarbon-based chain" means a branched hydrocarbon-based chain which can also form one to five 3- to 7-membered carbon-based rings, this chain possibly comprising one to three unsaturations, i.e. one to three double bonds and/or triple bonds.

The term "$C_2$-$C_4$ (poly)hydroxyalkoxy" means a $C_2$-$C_4$ alkoxy group substituted with 1 or 2 hydroxyl groups.

For the purposes of the present invention, the expression "$C_2$-$C_4$ (poly)hydroxyalkylamino" means an alkylamino group substituted with 1 or 2 hydroxyl groups.

The expression according to which the hydrocarbon-based chain may be interrupted with one or more oxygen, nitrogen or sulfur atoms or with an $SO_2$ radical, or according to which this chain is unsaturated, means that the carbon-based chain may be modified in the following manner:

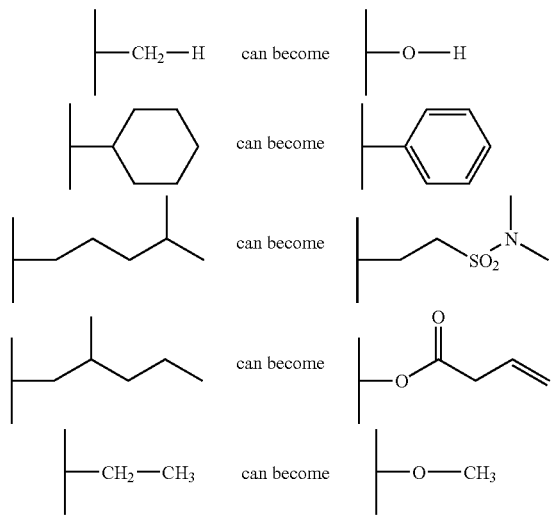

For the purposes of the present patent application, an organic or mineral anion is chosen, for example, from a halide such as chloride, bromide, fluoride or iodide; a hydroxide; a sulfate; a hydrogen sulfate; a ($C_1$-$C_6$)alkyl sulfate, for instance a methyl sulfate or an ethyl sulfate; an acetate; a tartrate; an oxalate; a ($C_1$-$C_6$)alkylsulfonate such as methyl sulfonate; an arylsulfonate, which is unsubstituted or substituted with a $C_1$-$C_4$ alkyl radical, for instance a 4-tolylsulfonate.

Preferably, $R_0$ represents a hydrogen atom; a linear or branched $C_1$-$C_6$ alkyl radical, which is unsubstituted or substituted with one to three radicals chosen from hydroxyl, $C_1$-$C_2$ alkoxy, $C_2$-$C_4$ (poly)hydroxyalkoxy, amino, $C_1$-$C_2$(di)alkylamino, $C_2$-$C_4$ (poly)hydroxyalkylamino, carboxyl and sulfonic radicals; a phenyl radical, which is unsubstituted or substituted with one to three radicals chosen from hydroxyl, $C_1$-$C_2$ alkoxy, $C_2$-$C_4$ (poly)hydroxyalkoxy, amino, $C_1$-$C_2$ (di)alkylamino, carboxyl and sulfonic radicals or a halogen atom such as chlorine, fluorine or bromine, an optionally cationic heteroaryl radical chosen from pyrazolyl, pyrrolyl, imidazolyl, thiazolyl, oxazolyl, triazolyl, pyridyl, pyrimidinyl, triazinyl, pyrazinyl and pyridazinyl radicals.

Even more preferably, $R_0$ preferably represents a hydrogen atom; a linear or branched $C_1$-$C_3$ alkyl radical, which is unsubstituted or substituted with one or two radicals chosen from hydroxyl, $C_1$-$C_2$ alkoxy, amino, $C_1$-$C_2$ (di)alkylamino, carboxyl and sulfonic radicals; a phenyl radical, which is unsubstituted or substituted with one or two radicals chosen from hydroxyl, amino, $C_1$-$C_2$ (di)alkylamino and $C_2$-$C_4$ (poly)hydroxyalkylamino radicals, or an optionally cationic heteroaryl radical chosen from pyrazolyl, pyrrolyl, imidazolyl and pyridyl radicals.

According to one particularly preferred embodiment, $R_0$ represents a hydrogen atom; a methyl, ethyl, propyl, butyl, 2-hydroxyethyl, 2-aminoethyl, 1-carboxymethyl, 2-carboxyethyl, 2-sulfonylethyl or 2-methoxyethyl; a phenyl radical, which is unsubstituted or substituted with one or two radicals chosen from amino, $C_1$-$C_2$ (di)alkylamino and $C_2$-$C_4$ (poly)hydroxyalkylamino radicals, or an optionally cationic heteroaryl radical chosen from pyrazolyl, pyrrolyl, imidazolyl and pyridyl radicals.

$R_0$ represents a hydrogen atom; a methyl, ethyl or 2-methoxyethyl radical; a phenyl radical, which is unsubstituted or substituted with an amino, (di)methylamino or (di) (2-hydroxyethyl)amino radical, or an optionally cationic heteroaryl radical chosen from imidazolyl and pyridyl radicals.

$R_2$, $R_6$, $R_{10}$ and $R_{16}$ preferably represent a hydrogen atom, a phenyl radical or a $C_1$-$C_4$ alkyl radical, which is unsubstituted or substituted with one or two radicals chosen from hydroxyl, amino, $C_1$-$C_2$ (di)alkylamino and carboxyl radicals.

According to one particularly preferred embodiment, $R_2$, $R_6$, $R_{10}$ and $R_{16}$ preferably represent a hydrogen atom, a methyl, phenyl or 2-hydroxymethyl radical, a carboxyl or a phenyl radical.

$R_1$, $R_4$, $R_5$, $R_7$, $R_9$, $R_{15}$, $R_{21}$ and $R_{22}$ preferably represent a $C_1$-$C_4$ alkyl radical, which is unsubstituted or substituted with one or two radicals chosen from hydroxyl, $C_1$-$C_2$ alkoxy, amino, $C_1$-$C_2$ (di)alkylamino, carboxyl and sulfonic radicals.

According to one particularly preferred embodiment, $R_1$, $R_4$, $R_5$, $R_7$, $R_9$, $R_{15}$, $R_{21}$ and $R_{22}$ preferably represent a methyl, ethyl, 2-hydroxyethyl, 1-carboxymethyl, 2-carboxyethyl or 2-sulfonylethyl radical.

$R_3$, $R_8$, $R_{11}$, $R_{12}$, $R_{13}$, $R_{14}$, $R_{17}$, $R_{18}$, $R_{19}$ and $R_{20}$ preferably represent, independently of each other, a hydrogen atom; a linear or branched $C_1$-$C_4$ alkyl radical, which is unsubstituted or substituted with one or two radicals chosen from hydroxyl, $C_1$-$C_2$ alkoxy, $C_2$-$C_4$(poly)hydroxyalkoxy, amino, $C_1$-$C_2$ (di) alkylamino, carboxyl and sulfonic radicals; a phenyl radical, which is unsubstituted or substituted with one or two radicals chosen from hydroxyl, $C_1$-$C_2$ alkoxy, $C_2$-$C_4$(poly)hydroxyalkoxy, amino, $C_1$-$C_2$(di)alkylamino, carboxyl and sulfonic radicals or a halogen atom such as chlorine, fluorine or bromine; a sulfonylamino radical; a $C_2$-$C_4$ (poly)hydroxyalkylamino radical.

More preferably, $R_3$, $R_8$, $R_{11}$, $R_{12}$, $R_{13}$, $R_{14}$, $R_{17}$, $R_{18}$, $R_{19}$ and $R_{20}$ represent a hydrogen atom, a $C_1$-$C_4$ alkyl radical, which is unsubstituted or substituted with one or two radicals chosen from hydroxyl radicals or a $C_1$-$C_2$ alkoxy radical; an amino radical; a $C_1$-$C_2$ (di)alkylamino radical; a carboxyl radical; a $C_2$-$C_4$ (poly)hydroxyalkylamino radical.

According to one particularly preferred embodiment, $R_3$, $R_8$, $R_{11}$, $R_{12}$, $R_{13}$, $R_{14}$, $R_{17}$, $R_{18}$, $R_{19}$ and $R_{20}$ represent, independently of each other, a hydrogen atom, a methyl or 2-hydroxymethyl radical, a carboxyl, a methoxy, ethoxy or 2-hydroxyethyloxy radical, or an amino, methylamino, dimethylamino or 2-hydroxyethylamino radical.

The compounds of formula (I) preferably used are those for which, in formula (I), $W_1$ is a 2-benzimidazolium radical and $W_2$ is a 2-benzimidazole radical. Even more preferably, they are the following compounds:

- 2-[5-(1,3-dimethyl-2-benzimidazolidene)-1-formazano]-1,3-dimethylbenzimidazolium chloride
- 2-[5-(1,3-dimethyl-2-benzimidazolidene)-3-methyl-1-formazano]-1,3-dimethylbenzimidazolium chloride
- 2-[5-(1,3-dimethyl-2-benzimidazolidene)-3-ethyl-1-formazano]-1,3-dimethylbenzimidazolium chloride
- 2-[5-(1,3-dimethyl-2-benzimidazolidene)-3-isopropyl-1-formazano]-1,3-dimethylbenzimidazolium chloride
- 2-[5-(1,3-dimethyl-2-benzimidazolidene)-3-phenyl-1-formazano]-1,3-dimethylbenzimidazolium chloride
- 2-[5-(1,3-dimethyl-2-benzimidazolidene)-3-(4'-methoxyphenyl)-1-formazano]-1,3-dimethylbenzimidazolium chloride
- 2-[5-(1,3-dimethyl-2-benzimidazolidene)-3-(4'-hydroxyphenyl)-1-formazano]-1,3-dimethylbenzimidazolium chloride
- 2-[5-(1,3-dimethyl-2-benzimidazolidene)-3-(4'-N,N-dimethylaminophenyl)-1-formazano]-1,3-dimethylbenzimidazolium chloride
- 2-[5-(1,3-dihydroxyethyl-2-benzimidazolidene)-1-formazano]-1,3-dihydroxyethylbenzimidazolium chloride
- 2-[5-(1,3-dihydroxyethyl-2-benzimidazolidene)-3-methyl-1-formazano]-1,3-dihydroxyethylbenzimidazolium chloride
- 2-[5-(1,3-dihydroxyethyl-2-benzimidazolidene)-3-ethyl-1-formazano]-1,3-dihydroxyethylbenzimidazolium chloride
- 2-[5-(1,3-dihydroxyethyl-2-benzimidazolidene)-3-phenyl-1-formazano]-1,3-dihydroxyethylbenzimidazolium chloride
- 2-[5-(1,3-dihydroxyethyl-2-benzimidazolidene)-3-isopropyl-1-formazano]-1,3-dihydroxyethylbenzimidazolium chloride
- 2-[5-(1,3-dihydroxyethyl-2-benzimidazolidene)-3-(4'-methoxyphenyl)-1-formazano]-1,3-dihydroxyethylbenzimidazolium chloride
- 2-[5-(1,3-dihydroxyethyl-2-benzimidazolidene)-3-(4'-hydroxyphenyl)-1-formazano]-1,3-dihydroxyethylbenzimidazolium chloride
- 2-[5-(1,3-dihydroxyethyl-2-benzimidazolidene)-3-(4'-N,N-dimethylaminophenyl)-1-formazano]-1,3-dihydroxyethylbenzimidazolium chloride
- 2-[5-(1,3-dicarboxyethyl-2-benzimidazolidene)-1-formazano]-1,3-dicarboxyethylbenzimidazolium chloride
- 2-[5-(1,3-dicarboxyethyl-2-benzimidazolidene)-3-methyl-1-formazano]-1,3-dicarboxyethylbenzimidazolium chloride
- 2-[5-(1,3-dicarboxyethyl-2-benzimidazolidene)-3-ethyl-1-formazano]-1,3-dicarboxyethylbenzimidazolium chloride
- 2-[5-(1,3-dicarboxyethyl-2-benzimidazolidene)-3-phenyl-1-formazano]-1,3-dicarboxyethylbenzimidazolium chloride
- 2-[5-(1,3-dicarboxyethyl-2-benzimidazolidene)-3-isopropyl-1-formazano]-1,3-dicarboxyethylbenzimidazolium chloride
- 2-[5-(1,3-dicarboxyethyl-2-benzimidazolidene)-3-(4'-methoxyphenyl)-1-formazano]-1,3-dicarboxyethylbenzimidazolium chloride
- 2-[5-(1,3-dicarboxyethyl-2-benzimidazolidene)-3-(4'-hydroxyphenyl)-1-formazano]-1,3-dicarboxyethylbenzimidazolium chloride
- 2-[5-(1,3-dicarboxyethyl-2-benzimidazolidene)-3-(4'-N,N-dimethylaminophenyl)-1-formazano]-1,3-dicarboxyethylbenzimidazolium chloride A second subject of the present invention consists of a composition for dyeing keratin fibers, in particular human keratin fibers and more particularly the hair, comprising, in a medium that is suitable for dyeing, at least one compound of formula (I) as a direct dye.

Preferably, the compounds of formula (I) are present in the composition according to the present invention in a weight concentration ranging from 0.001% to 5% and preferably from 0.05% to 2% relative to the total weight of the composition.

According to one variant, the composition according to the present invention also comprises at least one direct dye other than those of formula (I) according to the invention, chosen especially from the group formed by neutral, acidic or cationic nitrobenzene direct dyes, neutral, acidic or cationic azo direct dyes, neutral, acidic or cationic quinone and in particular anthraquinone direct dyes, azine direct dyes, methine direct dyes, triarylmethane direct dyes, indoamine dyes and natural direct dyes. The additional direct dye(s) preferably represent(s) from 0.001% to 20% by weight approximately and even more preferably from 0.005% to 10% by weight approximately relative to the total weight of the composition.

The composition of the invention may also comprise an oxidizing agent. This oxidizing agent may be any oxidizing agent used conventionally for dyeing or bleaching keratin fibers. The oxidizing agent is preferably chosen from hydrogen peroxide, urea peroxide, alkali metal bromates, persalts such as perborates and persulfates, peracids and enzymes, among which mention may be made of 2-electron oxidoreductases such as uricases, peroxidases and 4-electron oxidoreductases, for instance laccases. It is particularly preferred to use hydrogen peroxide as oxidizing agent.

The composition according to the invention may also comprise an oxidation base. This oxidation base may be chosen from the oxidation bases conventionally used in oxidation dyeing, for example para-phenylenediamines, bis(phenyl)alkylenediamines, para-aminophenols, ortho-aminophenols and heterocyclic bases.

The composition according to the invention may also contain one or more couplers conventionally used for dyeing keratin fibers. Among these couplers, mention may be made especially of meta-phenylenediamines, meta-aminophenols, meta-diphenols, naphthalene-based couplers and heterocyclic couplers.

In the composition of the present invention, the coupler(s) is (are) generally present in an amount ranging from 0.001% to 10% by weight approximately and more preferably from 0.005% to 6% relative to the total weight of the dye composition. The oxidation base(s) is (are) present in an amount preferably ranging from 0.001% to 10% by weight approximately and more preferably from 0.005% to 6% by weight approximately relative to the total weight of the dye composition.

In general, the addition salts with an acid that may be used in the context of the dye compositions of the invention for the oxidation bases and couplers are chosen especially from the hydrochlorides, hydrobromides, sulfates, citrates, succinates, tartrates, lactates, tosylates, benzenesulfonates, phosphates and acetates.

The medium that is suitable for dyeing, also known as the dye support, generally consists of water or of a mixture of water and of at least one organic solvent to dissolve the compounds that would not be sufficiently water-soluble. Examples of organic solvents that may be mentioned include $C_1$-$C_4$ lower alkanols such as ethanol and isopropanol, polyols and polyol ethers, for instance 2-butoxyethanol, propylene glycol, propylene glycol monomethyl ether, diethylene glycol monoethyl ether and monomethyl ether, and also aromatic alcohols, for instance benzyl alcohol or phenoxyethanol, and mixtures thereof.

The organic solvents may be present in proportions preferably of between 1% and 40% by weight approximately and even more preferably between 5% and 30% by weight approximately relative to the total weight of the dye composition.

The dye composition in accordance with the invention may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric associative polymers, antioxidants, penetrating agents, sequestering agents, fragrances, buffers, dispersants, conditioning agents, for instance volatile or nonvolatile, modified or unmodified silicones, film-forming agents, ceramides, preserving agents and opacifiers.

The adjuvants mentioned above are generally present in an amount for each of between 0.01% and 20% by weight relative to the weight of the composition.

Needless to say, a person skilled in the art will take care to select this or these optional additional compound(s) such that the advantageous properties intrinsically associated with the dye composition in accordance with the invention are not, or are not substantially, adversely affected by the envisaged addition(s).

The pH of the dye composition in accordance with the invention is generally between 3 and 12 approximately and preferably between 5 and 11 approximately. It may be adjusted to the desired value by means of acidifying or basifying agents usually used in the dyeing of keratin fibers, or alternatively using standard buffer systems.

Among the acidifying agents that may be mentioned, for example, are mineral or organic acids, for instance hydrochloric acid, orthophosphoric acid, sulfuric acid, carboxylic acids, for instance acetic acid, tartaric acid, citric acid and lactic acid, and sulfonic acids.

Among the basifying agents that may be mentioned, for example, are aqueous ammonia, alkali metal carbonates, alkanolamines such as monoethanolamine, diethanolamine and triethanolamine and derivatives thereof, sodium hydroxide, potassium hydroxide and the compounds of formula (III) below:

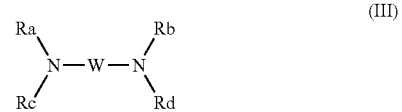

(III)

in which W is a propylene residue optionally substituted with a hydroxyl group or a $C_1$-$C_4$ alkyl radical, $R_a$, $R_b$, $R_c$ and $R_d$, which may be identical or different, represent a hydrogen atom or a $C_1$-$C_4$ alkyl or $C_1$-$C_4$ hydroxyalkyl radical.

The dye composition according to the invention may be in various forms, such as in the form of liquids, creams or gels or in any other form that is suitable for dyeing keratin fibers and especially human hair.

A third subject of the present invention consists of a direct dyeing process, which comprises the application of a dye composition comprising at least one dye of formula (I) as defined above to keratin fibers, in particular human keratin fibers and more particularly the hair, for a time that is sufficient to develop the desired coloration. The fibers are then rinsed and then dried.

The composition containing the dye of formula (I) may be applied to the keratin fibers in the presence of an oxidizing agent, which brings about the bleaching of the fiber (lightening direct dyeing process). This oxidizing agent may be added to the composition containing the dye of formula (I) at the time of use or directly onto the keratin fiber.

A subject of the invention is also an oxidation dyeing process, which comprises the application to the fibers of a dye composition comprising at least one dye of formula (I), at least one oxidation base and optionally at least one coupler, in the presence of an oxidizing agent.

The oxidation base, the coupler and the oxidizing agent are as defined above.

The color may be revealed at acid, neutral or alkaline pH and the oxidizing agent may be added to the composition according to the invention just at the time of use, or it may be used starting with an oxidizing composition containing it, in which case it is applied to the fibers simultaneously with or sequentially to the dye composition.

In the case of the lightening direct dyeing or oxidation dyeing, the dye composition is mixed, preferably at the time of use, with a composition containing, in a medium that is suitable for dyeing, at least one oxidizing agent, this oxidizing agent being present in an amount that is sufficient to develop a coloration. The mixture obtained is then applied to the keratin fibers. After a leave-in time of 3 to 50 minutes approximately and preferably 5 to 30 minutes approximately, the keratin fibers are rinsed, washed with shampoo, rinsed again and then dried.

The oxidizing composition may also contain various adjuvants conventionally used in compositions for dyeing the hair, and as defined above.

The pH of the oxidizing composition containing the oxidizing agent is such that, after mixing with the dye composition, the pH of the resulting composition applied to the keratin fibers preferably ranges between 3 and 12 approximately and even more preferably between 5 and 11. It may be adjusted to the desired value using acidifying or basifying agents usually used in the dyeing of keratin fibers, and as defined above.

The composition that is finally applied to the keratin fibers may be in various forms, such as in the form of liquids, creams or gels or in any other form that is suitable for dyeing keratin fibers, and especially human hair.

A subject of the present invention is, furthermore, a process of bleaching of the direct dyes, which form the subject of the invention and which have just been described. Advantageously, this bleaching process may be applied to keratin fibers that have been dyed beforehand in accordance with the dyeing processes that have just been described. One of the advantages of this process is that the natural color of the fibers before dyeing with the composition according to the invention is conserved, and only the color provided by the direct dye is removed.

This process also has the advantage of being quick and easy to perform. Thus, the process consists in applying to the compound of formulae (I) and (I') a bleaching composition comprising at least one reducing agent chosen from reducing agents comprising sulfur. When the process is applied to keratin fibers, it consists in performing the following steps:

a) a bleaching composition comprising, in a suitable medium, at least one reducing agent chosen from reducing agents comprising sulfur is applied to the fibers which have been treated beforehand with a dye composition according to the invention;
b) this composition is left to act for a time that is sufficient for the bleaching to take place;
c) the fibers are optionally rinsed;
d) the fibers are washed, rinsed and then dried.

By way of example, the reducing agents comprising sulfur are chosen from compounds containing at least one thiol, sulfide or sulfite function.

Among the thiols that may be used as reducing compounds, mention may be made of thioglycolic acid, thiolactic acid, the alkali metal or alkaline-earth metal salts thereof (for instance the sodium, potassium or calcium salts) and esters thereof; β-mercaptoethanol, cysteine, cysteamine and derivatives thereof; homocysteine and a salt thereof; mercaptoaldehydes; penicillamine; glutathione. These compounds may be used alone or as mixtures.

As regards the sulfites that may be used as reducing agents, among which are also featured bisulfites and hydrosulfites, the alkali metal, alkaline-earth metal or ammonium salts, and also mixtures thereof, are suitable. Mention may be made more particularly of sodium sulfite, sodium metasulfite and sodium hydrosulfite.

As regards the sulfides, among which are also featured disulfides, mention may be made especially of cystine.

The content of reducing agent in the composition is advantageously between 0.01% and 10% by weight of the dye-bleaching composition and preferably between 0.1% and 5% by weight of the said bleaching composition.

The medium of the composition conventionally comprises water or an organic solvent. Everything that has been stated hereinabove regarding the medium of the dye composition remains valid, and reference may be made thereto.

The composition may similarly comprise conventional adjuvants such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric associative polymers, antioxidants, penetrating agents, sequestering agents, fragrances, buffers, dispersants, conditioning agents, for instance volatile or nonvolatile, modified or unmodified silicones, film-forming agents, ceramides, preserving agents and opacifiers.

The adjuvants mentioned above are generally present in an amount for each of between 0.01% and 20% by weight relative to the weight of the bleaching composition. Needless to say, a person skilled in the art will take care to select this or these optional adjuvant(s) such that the advantageous properties intrinsically associated with the use of the bleaching composition are not, or are not substantially, adversely affected by the envisaged addition(s).

The pH of the bleaching composition is generally between 6 and 10 and advantageously between 7 and 9. It may be adjusted to the desired value by means of acidifying or basifying agents usually used in the field, lists of which have been given hereinabove, or alternatively using standard buffer systems.

The bleaching composition may be applied to either dry hair or wet hair.

As a guide, the temperature at which the bleaching process is performed is between 15 and 50° C. and preferably in the region of room temperature.

The leave-in time for the composition is generally between 1 and 30 minutes and more particularly between 2 and 20 minutes. It should be noted that this range is given merely as a guide. Specifically, it may be determined without difficulty by a person skilled in the art, the bleaching of the hair being able to be observed visually, since the phenomenon is visible. Generally, the larger the content of reducing agent and/or the higher the temperature, the shorter the leave-in time to bleach the dye or the hair that has been dyed beforehand with the dyes according to the invention.

The present invention also relates to the tetraazepentamethine compounds of formula (I')

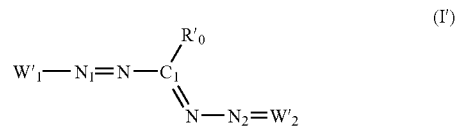

in which
W'$_1$ represents a cationic heteroaromatic radical of formula (II') or (III'):

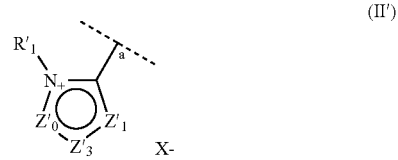

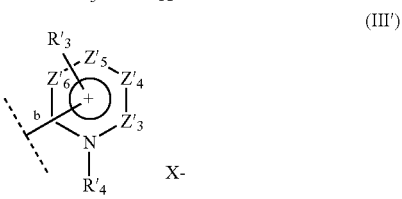

W'$_2$ represents a heteroaromatic radical of formula (IV') or (V'):

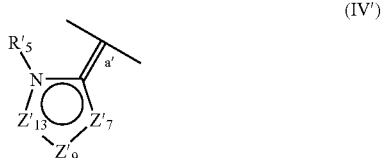

-continued

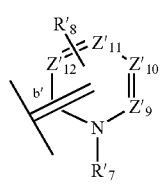
(V')

in which:
- $Z'_0$ represents a radical $CR'_2$, a nitrogen atom or a radical $NR'_{21}$,
- $Z'_1$, represents an oxygen atom or a radical $NR'_9$,
- $Z'_2$ represents a nitrogen atom or a radical $CR'_{10}$,
- $Z'_3$ represents a nitrogen atom or a radical $CR'_{11}$,
- $Z'_4$ represents a nitrogen atom or a radical $CR'_{12}$,
- $Z'_5$ represents a nitrogen atom or a radical $CR'_{13}$,
- $Z'_6$ represents a nitrogen atom or a radical $CR'_{14}$,
- $Z'_7$ represents an oxygen atom or a radical $NR'_{15}$,
- $Z'_8$ represents a nitrogen atom or a radical $CR'_{16}$,
- $Z'_9$ represents a nitrogen atom or a radical $CR'_{17}$,
- $Z'_{10}$ represents a nitrogen atom or a radical $CR'_{18}$,
- $Z'_{11}$ represents a nitrogen atom or a radical $CR'_{19}$,
- $Z'_{12}$ represents a nitrogen atom or a radical $CR'_{20}$,
- $Z'_{13}$ represents a radical $CR'_6$, a nitrogen atom or a radical $NR'_{22}$,
- it being understood that each of the rings of formulae (II'), (III'), (IV') and (V') comprise not more than three nitrogen atoms and that two of the three nitrogen atoms may be contiguous,
- the bond a of the 5-membered cationic heteroaromatic radical of formula (II') being linked to the nitrogen atom $N_1$ of formula (I'),
- the bond b of the 6-membered cationic heteroaromatic radical of formula (III') being linked to the nitrogen atom $N_1$ of formula (I'),
- the double bond a' of the 5-membered heteroaromatic radical of formula (IV') being linked to the nitrogen atom $N_2$ of formula (I'),
- the double bond b' of the 6-membered heteroaromatic radical of formula (VI) being linked to the nitrogen atom $N_2$ of formula (I'),
- the bond b, linking the cationic heteroaromatic radical of formula (III') to the nitrogen atom $N_1$ of formula (I'), being in an ortho or para position relative to the nitrogen atom bearing the radical $R'_4$ when $Z'_5$ represents a radical $CR'_{13}$;
- the bond b being in an ortho position relative to the nitrogen atom bearing the radical $R'_4$ when $Z'_5$ represents a nitrogen atom,
- the bond b', linking the heteroaromatic radical of formula (V') to the nitrogen atom $N_2$ of formula (I'), being in an ortho or para position relative to the nitrogen atom bearing the radical $R'_7$ when $Z'_{11}$ represents a radical $CR'_{19}$; the bond b' being in an ortho position relative to the nitrogen atom bearing the radical $R'_7$ when $Z'_{11}$ represents a nitrogen atom,
- $R'_2$, $R'_6$, $R'_{10}$ and $R'_{16}$ represent, independently of each other, a hydrogen atom; a linear or branched $C_1$-$C_4$ alkyl radical, which is unsubstituted or substituted with one to three radicals chosen from hydroxyl, $C_1$-$C_2$ alkoxy, $C_2$-$C_4$ (poly)hydroxyalkoxy, amino, $C_1$-$C_2$ (di)alkylamino, carboxyl and sulfonic radicals; a phenyl radical, which is unsubstituted or substituted with one or two radicals chosen from hydroxyl, $C_1$-$C_2$ alkoxy, $C_2$-$C_4$ (poly)hydroxyalkoxy, amino and $C_1$-$C_2$ (di)alkylamino radicals; a carboxyl radical; a sulfonylamino radical,
- $R'_1$, $R'_4$, $R'_5$, $R'_7$, $R'_9$, $R'_{15}$, $R'_{21}$ and $R'_{22}$ represent, independently of each other, a linear or branched $C_1$-$C_8$ alkyl radical, which is unsubstituted or substituted with one to three radicals chosen from hydroxyl, $C_1$-$C_2$ alkoxy, $C_2$-$C_4$ (poly)hydroxyalkoxy, amino, $C_1$-$C_2$ (di)alkylamino, carboxyl and sulfonic radicals;
- $R'_0$, $R'_3$, $R'_8$, $R'_{11}$, $R'_{12}$, $R'_{13}$, $R'_{14}$, $R'_{17}$, $R'_{18}$, $R'_{19}$ and $R'_{20}$ represent, independently of each other, a hydrogen atom, a linear or branched $C_1$-$C_{16}$ hydrocarbon-based chain, this chain possibly being saturated or unsaturated with one to three unsaturations, this chain being unsubstituted or substituted with one to three radicals chosen from hydroxyl, $C_1$-$C_2$ alkoxy, $C_2$-$C_4$ (poly)hydroxyalkoxy, amino, $C_1$-$C_2$ (di)alkylamino, carboxyl, sulfonic, sulfonylamino and $C_2$-$C_4$ (poly)hydroxyalkylamino radicals or a halogen atom such as chlorine, fluorine or bromine; a phenyl radical, which is unsubstituted or substituted with one to three radicals chosen from hydroxyl, $C_1$-$C_2$ alkoxy, $C_2$-$C_4$ (poly)hydroxyalkoxy, amino, $C_1$-$C_2$ (di)alkylamino, carboxyl, sulfonic, sulfonylamino and $C_2$-$C_4$ (poly)hydroxyalkylamino radicals or a halogen atom such as chlorine, fluorine or bromine; a heteroaryl radical chosen from pyrazolyl, pyrrolyl, imidazolyl, thiazolyl, oxazolyl, triazolyl, pyridyl, pyrimidinyl, triazinyl, pyrazinyl and pyridazinyl radicals; in addition, this hydrocarbon-based chain may be interrupted with one or two oxygen, nitrogen or sulfur atoms or with an $SO_2$ radical,
- $R'_2$ with $R'_{10}$, $R'_{11}$ with $R'_{12}$, $R'_6$ with $R'_{16}$, and $R'_{17}$ with $R'_{18}$ being able to form, independently of each other, a 5- or 6-membered carbon-based aromatic ring, which is unsubstituted or substituted with one or two hydroxyl, amino, (di) $(C_1$-$C_2)$alkylamino, $C_1$-$C_2$ alkoxy or $C_2$-$C_4$ (poly)hydroxyalkylamino radicals, subject to $W'_1$ and $W'_2$ not representing, simultaneously, the same bicyclic system, it being understood that $R'_0$, $R'_3$, $R'_8$, $R'_{11}$, $R'_{12}$, $R'_{13}$, $R'_{14}$, $R'_{17}$, $R'_{18}$, $R'_{19}$ and $R'_{20}$ do not comprise a peroxide bond or diazo or nitroso radicals,
- X is an organic or mineral anion.

Preferably, $R'_0$ represents a hydrogen atom; a linear or branched $C_1$-$C_6$ alkyl radical, which is unsubstituted or substituted with one to three radicals chosen from hydroxyl, $C_1$-$C_2$ alkoxy, $C_2$-$C_4$ (poly)hydroxyalkoxy, amino, $C_1$-$C_2$ (di) alkylamino, $C_2$-$C_4$ (poly)hydroxyalkylamino, carboxyl and sulfonic radicals; a phenyl radical, which is unsubstituted or substituted with one to three radicals chosen from hydroxyl, $C_1$-$C_2$ alkoxy, $C_2$-$C_4$ (poly)hydroxyalkoxy, amino, $C_1$-$C_2$ (di) alkylamino, carboxyl and sulfonic radicals or a halogen atom such as chlorine, fluorine or bromine; an optionally cationic heteroaryl radical chosen from pyrazolyl, pyrrolyl, imidazolyl, thiazolyl, oxazolyl, triazolyl, pyridyl, pyrimidinyl, triazinyl, pyrazinyl and pyridazinyl radicals.

Even more preferably, $R'_0$ preferably represents a hydrogen atom; a linear or branched $C_1$-$C_3$ alkyl radical, which is unsubstituted or substituted with one or two radicals chosen from hydroxyl, $C_1$-$C_2$ alkoxy, amino, $C_1$-$C_2$ (di)alkylamino, carboxyl and sulfonic radicals; a phenyl radical, which is unsubstituted or substituted with one or two radicals chosen from hydroxyl, amino, $C_1$-$C_2$ (di)alkylamino and $C_2$-$C_4$ (poly)hydroxyalkylamino radicals, or an optionally cationic heteroaryl radical chosen from pyrazolyl, pyrrolyl, imidazolyl and pyridyl radicals.

According to one particularly preferred embodiment, $R'_0$ represents a hydrogen atom; a methyl, ethyl, propyl, butyl, 2-hydroxyethyl, 2-aminoethyl, 1-carboxymethyl, 2-carboxyethyl, 2-sulfonylethyl or 2-methoxyethyl; a phenyl radical, which is unsubstituted or substituted with one or two radicals chosen from amino, $C_1$-$C_2$ (di)alkylamino and $C_2$-$C_4$ (poly) hydroxyalkylamino radicals, or an optionally cationic heteroaryl radical chosen from pyrazolyl, pyrrolyl, imidazolyl and pyridyl radicals.

$R'_0$ represents a hydrogen atom; a methyl, ethyl or 2-methoxyethyl radical; a phenyl radical, which is unsubstituted or substituted with an amino, (di)methylamino or (di)(2-hydroxyethyl)amino radical, or an optionally cationic heteroaryl radical chosen from pyrazolyl, pyrrolyl, imidazolyl and pyridyl radicals.

$R'_2$, $R'_6$, $R'_{10}$ and $R'_{16}$ preferably represent a hydrogen atom, a $C_1$-$C_4$ alkyl radical, which is unsubstituted or substituted with one or two radicals chosen from hydroxyl, amino, $C_1$-$C_2$ (di)alkylamino and carboxyl radicals, or a phenyl radical.

According to one particularly preferred embodiment, $R'_2$, $R'_6$, $R'_{10}$ and $R'_{16}$ preferably represent a hydrogen atom, a methyl, phenyl or 2-hydroxymethyl radical or a carboxyl.

$R'_1$, $R'_4$, $R'_5$, $R'_7$, $R'_9$, $R'_{15}$, $R'_{21}$ and $R'_{22}$ preferably represent a $C_1$-$C_4$ alkyl radical, which is unsubstituted or substituted with one or two radicals chosen from hydroxyl, $C_1$-$C_2$ alkoxy, amino, $C_1$-$C_2$ (di)alkylamino, carboxyl and sulfonic radicals.

According to one particularly preferred embodiment, $R'_1$, $R'_4$, $R'_5$, $R'_7$, $R'_9$, $R'_{15}$, $R'_{21}$ and $R'_{22}$ preferably represent a methyl, ethyl, 2-hydroxyethyl, 1-carboxymethyl, 2-carboxyethyl or 2-sulfonylethyl radical.

$R'_3$, $R'_8$, $R'_{11}$, $R'_{12}$, $R'_{13}$, $R'_{14}$, $R'_{17}$, $R'_{18}$, $R'_{19}$ and $R'_{20}$ preferably represent, independently of each other, a hydrogen atom; a linear or branched $C_1$-$C_4$ alkyl radical, which is unsubstituted or substituted with one or two radicals chosen from hydroxyl, $C_1$-$C_2$ alkoxy, $C_2$-$C_4$ (poly)hydroxyalkoxy, amino, $C_1$-$C_2$ (di)alkylamino, carboxyl and sulfonic radicals; a phenyl radical, which is unsubstituted or substituted with one or two radicals chosen from hydroxyl, $C_1$-$C_2$ alkoxy, $C_2$-$C_4$ (poly)hydroxyalkoxy, amino, $C_1$-$C_2$ (di)alkylamino, carboxyl and sulfonic radicals or a halogen atom such as chlorine, fluorine or bromine; a sulfonylamino radical; a $C_2$-$C_4$ (poly)hydroxyalkylamino radical.

More preferably, $R'_3$, $R'_8$, $R'_{11}$, $R'_{12}$, $R'_{13}$, $R'_{14}$, $R'_{17}$, $R'_{18}$, $R'_{19}$ and $R'_{20}$ represent a hydrogen atom, a $C_1$-$C_4$ alkyl radical, which is unsubstituted or substituted with one or two radicals chosen from hydroxyl radicals or a $C_1$-$C_2$ alkoxy radical; an amino radical; a $C_1$-$C_2$ (di)alkylamino radical; a carboxyl radical; a $C_2$-$C_4$ (poly)hydroxyalkylamino radical.

According to one particularly preferred embodiment, $R'_3$, $R'_8$, $R'_{11}$, $R'_{12}$, $R'_{13}$, $R'_{14}$, $R'_{17}$, $R'_{19}$ and $R'_{20}$ represent, independently of each other, a hydrogen atom, a methyl or 2-hydroxymethyl radical, a carboxyl, a methoxy, ethoxy or 2-hydroxyethyloxy radical, or an amino, methylamino, dimethylamino or 2-hydroxyethylamino radical.

A. Preferably, the compounds of formula (I') are chosen from the family defined by the compounds for which $W'_1$ is a 2-pyridinium radical and $W'_2$ is a 2-pyridine radical. Even more preferably, they are the following compounds:

2-[5-(N-methyl-2-pyridinylidene)-1-formazano]-N-methylpyridinium chloride

2-[5-(N-methyl-2-pyridinylidene)-3-methyl-1-formazano]-N-methylpyridinium chloride 2-[5-(N-methyl-2-pyridinylidene)-3-ethyl-1-formazano]-N-methylpyridinium chloride 2-[5-(N-methyl-2-pyridinylidene)-3-isopropyl-1-formazano]-N-methylpyridinium chloride 2-[5-(N-methyl-2-pyridinylidene)-3-phenyl-1-formazano]-N-methylpyridinium chloride 2-[5-(N-methyl-2-pyridinylidene)-3-(4'-methoxyphenyl)-1-formazano]-N-methylpyridinium chloride 2-[5-(N-methyl-2-pyridinylidene)-3-(4'-hydroxyphenyl)-1-formazano]-N-methylpyridinium chloride 2-[5-(N-methyl-2-pyridinylidene)-3-(4'-N,N-dimethylaminophenyl)-1-formazano]-N-methylpyridinium chloride 2-[5-(4-pyrrolidino-N-methyl-2-pyridinylidene)-1-formazano]-4-pyrrolidino-N-methylpyridinium chloride 2-[5-(4-pyrrolidino-N-methyl-2-pyridinylidene)-3-methyl-1-formazano]-4-pyrrolidino-N-methylpyridinium chloride 2-[5-(4-pyrrolidino-N-methyl-2-pyridinylidene)-3-ethyl-1-formazano]-4-pyrrolidino-N-methylpyridinium chloride 2-[5-(4-pyrrolidino-N-methyl-2-pyridinylidene)-3-isopropyl-1-formazano]-4-pyrrolidino-N-methylpyridinium chloride 2-[5-(4-pyrrolidino-N-methyl-2-pyridinylidene)-3-phenyl-1-formazano]-4-pyrrolidino-N-methylpyridinium chloride 2-[5-(4-pyrrolidino-N-methyl-2-pyridinylidene)-3-(4'-methoxyphenyl)-1-formazano]-4-pyrrolidino-N-methylpyridinium chloride 2-[5-(4-pyrrolidino-N-methyl-2-pyridinylidene)-3-(4'-hydroxyphenyl)-1-formazano]-4-pyrrolidino-N-methylpyridinium chloride 2-[5-(4-pyrrolidino-N-methyl-2-pyridinylidene)-3-(4'-N,N-dimethylaminophenyl)-1-formazano]-4-pyrrolidino-N-methylpyridinium chloride 2-[5-(N-hydroxyethyl-2-pyridinylidene)-1-formazano]-N-hydroxyethylpyridinium chloride 2-[5-(N-hydroxyethyl-2-pyridinylidene)-3-methyl-1-formazano]-N-hydroxyethylpyridinium chloride 2-[5-(N-hydroxyethyl-2-pyridinylidene)-3-ethyl-1-formazano]-N-hydroxyethylpyridinium chloride 2-[5-(N-hydroxyethyl-2-pyridinylidene)-3-phenyl-1-formazano]-N-hydroxyethylpyridinium chloride 2-[5-(N-hydroxyethyl-2-pyridinylidene)-3-(2-pyridinyl)-1-formazano]-N-hydroxyethylpyridinium bromide 2-[5-(N-hydroxyethyl-2-pyridinylidene)-3-(2-N-methylpyridinylium methosulfate)-1-formazano]-N-hydroxyethylpyridinium bromide 2-[5-(N-hydroxyethyl-2-pyridinylidene)-3-isopropyl-1-formazano]-N-hydroxyethylpyridinium chloride 2-[5-(N-hydroxyethyl-2-pyridinylidene)-3-(4'-methoxyphenyl)-1-formazano]-N-hydroxyethylpyridinium chloride 2-[5-(N-hydroxyethyl-2-pyridinylidene)-3-(4'-hydroxyphenyl)-1-formazano]-N-hydroxyethylpyridinium chloride 2-[5-(N-hydroxyethyl-2-pyridinylidene)-3-(4'-N,N-dimethylaminophenyl)-1-formazano]-N-hydroxyethylpyridinium chloride 2-[5-(N-carboxyethyl-2-pyridinylidene)-1-formazano]-N-carboxyethylpyridinium chloride 2-[5-(N-carboxyethyl-2-pyridinylidene)-3-methyl-1-formazano]-N-carboxyethylpyridinium chloride 2-[5-(N-carboxyethyl-2-pyridinylidene)-3-ethyl-1-formazano]-N-carboxyethylpyridinium chloride 2-[5-(N-carboxyethyl-2-pyridinylidene)-3-phenyl-1-formazano]-N-carboxyethylpyridinium chloride 2-[5-(N-carboxyethyl-2-pyridinylidene)-3-isopropyl-1-formazano]-N-carboxyethylpyridinium chloride 2-[5-(N-carboxyethyl-2-pyridinylidene)-3-(4'-methoxyphenyl)-1-formazano]-N-carboxyethylpyridinium chloride 2-[5-(N-carboxyethyl-2-pyridinylidene)-3-(4'-hydroxyphenyl)-1-formazano]-N-carboxyethylpyridinium chloride 2-[5-(N-carboxyethyl-2-pyridinylidene)-3-(4'-N,N-dimethylaminophenyl)-1-formazano]-N-carboxyethylpyridinium chloride B. Preferably, the compounds of formula (I') are chosen from the family defined by the compounds for which $W'_1$ is a 4-pyridinium radical and $W'_2$ is a 4-pyridine radical. Even more preferably, they are the following compounds:

4-[5-(N-methyl-4-pyridinylidene)-1-formazano]-N-methylpyridinium chloride

4-[5-(N-methyl-4-pyridinylidene)-3-methyl-1-formazano]-N-methylpyridinium chloride 4-[5-(N-methyl-4-pyridinylidene)-3-ethyl-1-formazano]-N-methylpyridinium chloride 4-[5-(N-methyl-4-pyridinylidene)-3-isopropyl-1-formazano]-N-methylpyridinium chloride 4-[5-(N-methyl-4-pyridinylidene)-3-phenyl-1-formazano]-N-methylpyridinium chloride 4-[5-(N-methyl-4-pyridinylidene)-3-(4'-methoxyphenyl)-1-formazano]-N-methylpyridinium chloride 4-[5-(N-methyl-4-pyridinylidene)-3-(4'-hydroxyphenyl)-1-formazano]-N-methylpyridinium chloride 4-[5-(N-methyl-4-pyridinylidene)-3-(4'-N,N-dimethylaminophenyl)-1-formazano]-N-methylpyridinium chloride 4-[5-(N-hydroxyethyl-4-pyridinylidene)-1-formazano]-N-hydroxyethylpyridinium chloride 4-[5-(N-hydroxyethyl-4-pyridinylidene)-3-methyl-1-formazano]-N-hydroxyethylpyridinium chloride 4-[5-(N-hydroxyethyl-4-pyridinylidene)-3-ethyl-1-formazano]-N-hydroxyethylpyridinium chloride 4-[5-(N-hydroxyethyl-4-pyridinylidene)-3-phenyl-1-formazano]-N-hydroxyethylpyridinium chloride 4-[5-(N-hydroxyethyl-4-pyridinylidene)-3-isopropyl-1-formazano]-N-hydroxyethylpyridinium chloride 4-[5-(N-hydroxyethyl-4-pyridinylidene)-3-(4'-methoxyphenyl)-1-formazano]-N-hydroxyethylpyridinium chloride 4-[5-(N-hydroxyethyl-4-pyridinylidene)-3-(4'-hydroxyphenyl)-1-formazano]-N-hydroxyethylpyridinium chloride 4-[5-(N-hydroxyethyl-4-pyridinylidene)-3-(4'-N,N-dimethylaminophenyl)-1-formazano]-N-hydroxyethylpyridinium chloride 4-[5-(N-carboxyethyl-4-pyridinylidene)-1-formazano]-N-carboxyethylpyridinium chloride 4-[5-(N-carboxyethyl-4-pyridinylidene)-3-methyl-1-formazano]-N-carboxyethylpyridinium chloride 4-[5-(N-carboxyethyl-4-pyridinylidene)-3-ethyl-1-formazano]-N-carboxyethylpyridinium chloride 4-[5-(N-carboxyethyl-4-pyridinylidene)-3-phenyl-1-formazano]-N-carboxyethylpyridinium chloride 4-[5-(N-carboxyethyl-4-pyridinylidene)-3-isopropyl-1-formazano]-N-carboxyethylpyridinium chloride 4-[5-(N-carboxyethyl-4-pyridinylidene)-3-(4'-methoxyphenyl)-1-formazano]-N-carboxyethylpyridinium chloride 4-[5-(N-carboxyethyl-4-pyridinylidene)-3-(4'-hydroxyphenyl)-1-formazano]-N-carboxyethylpyridinium chloride 4-[5-(N-carboxyethyl-4-pyridinylidene)-3-(4'-N,N-dimethylaminophenyl)-1-formazano]-N-carboxyethylpyridinium chloride C. Preferably, the compounds of formula (I') are chosen from the family defined by the compounds for which $W'_1$ is a 2-imidazolium radical and $W'_2$ is a 2-imidazole radical. Even more preferably, they are the following compounds:

2-[5-(1,3-dimethyl-2-imidazolidene)-1-formazano]-1,3-dimethylimidazolium chloride 2-[5-(1,3-dimethyl-2-imidazolidene)-3-methyl-1-formazano]-1,3-dimethylimidazolium chloride 2-[5-(1,3-dimethyl-2-imidazolidene)-3-ethyl-1-formazano]-1,3-dimethylimidazolium chloride 2-[5-(1,3-dimethyl-2-imidazolidene)-3-isopropyl-1-formazano]-1,3-dimethylimidazolium chloride 2-[5-(1,3-dimethyl-2-imidazolidene)-3-phenyl-1-formazano]-1,3-dimethylimidazolium chloride 2-[5-(1,3-dimethyl-2-imidazolidene)-3-(4'-methoxyphenyl)-1-formazano]-1,3-dimethylimidazolium chloride 2-[5-(1,3-dimethyl-2-imidazolidene)-3-(4'-hydroxyphenyl)-1-formazano]-1,3-dimethylimidazolium chloride 2-[5-(1,3-dimethyl-2-imidazolidene)-3-(4'-N,N-dimethylaminophenyl)-1-formazano]-1,3-dimethylimidazolium chloride 2-[5-(1,3-dihydroxyethyl-2-imidazolidene)-1-formazano]-1,3-dihydroxyethylimidazolium chloride 2-[5-(1,3-dihydroxyethyl-2-imidazolidene)-3-methyl-1-formazano]-1,3-dihydroxyethylimidazolium chloride 2-[5-(1,3-dihydroxyethyl-2-imidazolidene)-3-ethyl-1-formazano]-1,3-dihydroxyethylimidazolium chloride 2-[5-(1,3-dihydroxyethyl-2-imidazolidene)-3-phenyl-1-formazano]-1,3-dihydroxyethylimidazolium chloride 2-[5-(1,3-dihydroxyethyl-2-imidazolidene)-3-isopropyl-1-formazano]-1,3-dihydroxyethylimidazolium chloride 2-[5-(1,3-dihydroxyethyl-2-imidazolidene)-3-(4'-methoxyphenyl)-1-formazano]-1,3-dihydroxyethylimidazolium chloride 2-[5-(1,3-dihydroxyethyl-2-imidazolidene)-3-(4'-hydroxyphenyl)-1-formazano]-1,3-dihydroxyethylimidazolium chloride 2-[5-(1,3-dihydroxyethyl-2-imidazolidene)-3-(4'-N,N-dimethylaminophenyl)-1-formazano]-1,3-dihydroxyethylimidazolium chloride 2-[5-(1,3-dicarboxyethyl-2-imidazolidene)-1-formazano]-1,3-dicarboxyethylimidazolium chloride 2-[5-(1,3-dicarboxyethyl-2-imidazolidene)-3-methyl-1-formazano]-1,3-dicarboxyethylimidazolium chloride 2-[5-(1,3-dicarboxyethyl-2-imidazolidene)-3-ethyl-1-formazano]-1,3-dicarboxyethylimidazolium chloride 2-[5-(1,3-dicarboxyethyl-2-imidazolidene)-3-phenyl-1-formazano]-1,3-dicarboxyethylimidazolium chloride 2-[5-(1,3-dicarboxyethyl-2-imidazolidene)-3-isopropyl-1-formazano]-1,3-dicarboxyethylimidazolium chloride 2-[5-(1,3-dicarboxyethyl-2-imidazolidene)-3-(4'-methoxyphenyl)-1-formazano]-1,3-dicarboxyethylimidazolium chloride 2-[5-(1,3-dicarboxyethyl-2-imidazolidene)-3-(4'-hydroxyphenyl)-1-formazano]-1,3-dicarboxyethylimidazolium chloride 2-[5-(1,3-dicarboxyethyl-2-imidazolidene)-3-(4'-N,N-dimethylaminophenyl)-1-formazano]-1,3-dicarboxyethylimidazolium chloride D. Preferably, the compounds of formula (I') are chosen from the family defined by the compounds for which $W'_1$ is a 5-pyrazolium radical and $W'_2$ is a 5-pyrazole radical. Even more preferably, they are the following compounds:

5-[5-(1,2-dimethyl-5-pyrazolidene)-1-formazano]-1,2-dimethylpyrazolinium chloride
5-[5-(1,2-dimethyl-5-pyrazolidene)-3-methyl-1-formazano]-1,2-dimethylpyrazolinium chloride
5-[5-(1,2-dimethyl-5-pyrazolidene)-3-ethyl-1-formazano]-1,2-dimethylpyrazolinium chloride
5-[5-(1,2-dimethyl-5-pyrazolidene)-3-isopropyl-1-formazano]-1,2-dimethylpyrazolinium chloride
5-[5-(1,2-dimethyl-5-pyrazolidene)-3-phenyl-1-formazano]-1,2-dimethylpyrazolinium chloride
5-[5-(1,2-dimethyl-5-pyrazolidene)-3-(4'-methoxyphenyl)-1-formazano]-1,2-dimethylpyrazolinium chloride
5-[5-(1,2-dimethyl-5-pyrazolidene)-3-(4'-hydroxyphenyl)-1-formazano]-1,2-dimethylpyrazolinium chloride
5-[5-(1,2-dimethyl-5-pyrazolidene)-3-(4'-N,N-dimethylaminophenyl)-1-formazano]-1,2-dimethylpyrazolinium chloride
5-[5-(1,2-dihydroxyethyl-5-pyrazolidene)-1-formazano]-1,2-dihydroxyethylpyrazolinium chloride
5-[5-(1,2-dihydroxyethyl-5-pyrazolidene)-3-methyl-1-formazano]-1,2-dihydroxyethylpyrazolinium chloride
5-[5-(1,2-dihydroxyethyl-5-pyrazolidene)-3-ethyl-1-formazano]-1,2-dihydroxyethylpyrazolinium chloride
5-[5-(1,2-dihydroxyethyl-5-pyrazolidene)-3-phenyl-1-formazano]-1,2-dihydroxyethylpyrazolinium chloride
5-[5-(1,2-dihydroxyethyl-5-pyrazolidene)-3-isopropyl-1-formazano]-1,2-dihydroxyethylpyrazolinium chloride
5-[5-(1,2-dihydroxyethyl-5-pyrazolidene)-3-(4'-methoxyphenyl)-1-formazano]-1,2-dihydroxyethylpyrazolinium chloride
5-[5-(1,2-dihydroxyethyl-5-pyrazolidene)-3-(4'-hydroxyphenyl)-1-formazano]-1,2-dihydroxyethylpyrazolinium chloride
5-[5-(1,2-dihydroxyethyl-5-pyrazolidene)-3-(4'-N,N-dimethylaminophenyl)-1-formazano]-1,2-dihydroxyethylpyrazolinium chloride
5-[5-(1,2-dicarboxyethyl-5-pyrazolidene)-1-formazano]-1,2-dicarboxyethylpyrazolinium chloride
5-[5-(1,2-dicarboxyethyl-5-pyrazolidene)-3-methyl-1-formazano]-1,2-dicarboxyethylpyrazolinium chloride
5-[5-(1,2-dicarboxyethyl-5-pyrazolidene)-3-ethyl-1-formazano]-1,2-dicarboxyethylpyrazolinium chloride
5-[5-(1,2-dicarboxyethyl-5-pyrazolidene)-3-phenyl-1-formazano]-1,2-dicarboxyethylpyrazolinium chloride
5-[5-(1,2-dicarboxyethyl-5-pyrazolidene)-3-isopropyl-1-formazano]-1,2-dicarboxyethylpyrazolinium chloride
5-[5-(1,2-dicarboxyethyl-5-pyrazolidene)-3-(4'-methoxyphenyl)-1-formazano]-1,2-dicarboxyethylpyrazolinium chloride
5-[5-(1,2-dicarboxyethyl-5-pyrazolidene)-3-(4'-hydroxyphenyl)-1-formazano]-1,2-dicarboxyethylpyrazolinium chloride
5-[5-(1,2-dicarboxyethyl-5-pyrazolidene)-3-(4'-N,N-dimethylaminophenyl)-1-formazano]-1,2-dicarboxyethylpyrazolinium chloride E. Preferably, the compounds of formula (I') are chosen from the family defined by the compounds for which $W'_1$ is a 2-benzimidazolium radical and $W'_2$ is a 2-pyridine radical. Even more preferably, they are the following compounds:
2-[5-(N-methyl-2-pyridinylidene)-1-formazano]-1,3-dimethylbenzimidazolium chloride
2-[5-(N-methyl-2-pyridinylidene)-3-methyl-1-formazano]-1,3-dimethylbenzimidazolium chloride
2-[5-(N-methyl-2-pyridinylidene)-3-ethyl-1-formazano]-1,3-dimethylbenzimidazolium chloride
2-[5-(N-methyl-2-pyridinylidene)-3-isopropyl-1-formazano]-1,3-dimethylbenzimidazolium chloride
2-[5-(N-methyl-2-pyridinylidene)-3-phenyl-1-formazano]-1,3-dimethylbenzimidazolium chloride
2-[5-(N-methyl-2-pyridinylidene)-3-(4'-methoxyphenyl)-1-formazano]-1,3-dimethylbenzimidazolium chloride
2-[5-(N-methyl-2-pyridinylidene)-3-(4'-hydroxyphenyl)-1-formazano]-1,3-dimethylbenzimidazolium chloride
2-[5-(N-methyl-2-pyridinylidene)-3-(4'-N,N-dimethylaminophenyl)-1-formazano]-1,3-dimethylbenzimidazolium chloride
2-[5-(N-hydroxyethyl-2-pyridinylidene)-1-formazano]-1,3-dihydroxyethylbenzimidazolium chloride
2-[5-(N-hydroxyethyl-2-pyridinylidene)-3-methyl-1-formazano]-1,3-dihydroxyethylbenzimidazolium chloride
2-[5-(N-hydroxyethyl-2-pyridinylidene)-3-ethyl-1-formazano]-1,3-dihydroxyethylbenzimidazolium chloride
2-[5-(N-hydroxyethyl-2-pyridinylidene)-3-phenyl-1-formazano]-1,3-dihydroxyethylbenzimidazolium chloride
2-[5-(N-hydroxyethyl-2-pyridinylidene)-3-isopropyl-1-formazano]-1,3-dihydroxyethylbenzimidazolium chloride
2-[5-(N-hydroxyethyl-2-pyridinylidene)-3-(4'-methoxyphenyl)-1-formazano]-1,3-dihydroxyethylbenzimidazolium chloride
2-[5-(N-hydroxyethyl-2-pyridinylidene)-3-(4'-hydroxyphenyl)-1-formazano]-1,3-dihydroxyethylbenzimidazolium chloride
2-[5-(N-hydroxyethyl-2-pyridinylidene)-3-(4'-N,N-dimethylaminophenyl)-1-formazano]-1,3-dihydroxyethylbenzimidazolium chloride
2-[5-(N-carboxyethyl-2-pyridinylidene)-1-formazano]-1,3-dicarboxyethylbenzimidazolium chloride
2-[5-(N-carboxyethyl-2-pyridinylidene)-3-methyl-1-formazano]-1,3-dicarboxyethylbenzimidazolium chloride
2-[5-(N-carboxyethyl-2-pyridinylidene)-3-ethyl-1-formazano]-1,3-dicarboxyethylbenzimidazolium chloride
2-[5-(N-carboxyethyl-2-pyridinylidene)-3-phenyl-1-formazano]-1,3-dicarboxyethylbenzimidazolium chloride
2-[5-(N-carboxyethyl-2-pyridinylidene)-3-isopropyl-1-formazano]-1,3-dicarboxyethylbenzimidazolium chloride
2-[5-(N-carboxyethyl-2-pyridinylidene)-3-(4'-methoxyphenyl)-1-formazano]-1,3-dicarboxyethylbenzimidazolium chloride
2-[5-(N-carboxyethyl-2-pyridinylidene)-3-(4'-hydroxyphenyl)-1-formazano]-1,3-dicarboxyethylbenzimidazolium chloride
2-[5-(N-carboxyethyl-2-pyridinylidene)-3-(4'-N,N-dimethylaminophenyl)-1-formazano]-1,3-dicarboxyethylbenzimidazolium chloride F. Preferably, the compounds of formula (I') are chosen from the family defined by the compounds for which $W'_1$ is a 2-benzimidazolium radical and $W'_2$ is a 4-pyridine radical. Even more preferably, they are the following compounds:
2-[5-(N-methyl-4-pyridinylidene)-1-formazano]-1,3-dimethylbenzimidazolium chloride
2-[5-(N-methyl-4-pyridinylidene)-3-methyl-1-formazano]-1,3-dimethylbenzimidazolium chloride
2-[5-(N-methyl-4-pyridinylidene)-3-ethyl-1-formazano]-1,3-dimethylbenzimidazolium chloride
2-[5-(N-methyl-4-pyridinylidene)-3-isopropyl-1-formazano]-1,3-dimethylbenzimidazolium chloride
2-[5-(N-methyl-4-pyridinylidene)-3-phenyl-1-formazano]-1,3-dimethylbenzimidazolium chloride
2-[5-(N-methyl-4-pyridinylidene)-3-(4'-methoxyphenyl)-1-formazano]-1,3-dimethylbenzimidazolium chloride
2-[5-(N-methyl-4-pyridinylidene)-3-(4'-hydroxyphenyl)-1-formazano]-1,3-dimethylbenzimidazolium chloride 2-[5-(N-methyl-4-pyridinylidene)-3-(4'-N,N-dimethylaminophenyl)-1-formazano]-1,3-dimethylbenzimidazolium chloride
2-[5-(N-hydroxyethyl-4-pyridinylidene)-1-formazano]-1,3-dihydroxyethylbenzimidazolium chloride
2-[5-(N-hydroxyethyl-4-pyridinylidene)-3-methyl-1-formazano]-1,3-dihydroxyethylbenzimidazolium chloride
2-[5-(N-hydroxyethyl-4-pyridinylidene)-3-ethyl-1-formazano]-1,3-dihydroxyethylbenzimidazolium chloride
2-[5-(N-hydroxyethyl-4-pyridinylidene)-3-phenyl-1-formazano]-1,3-dihydroxyethylbenzimidazolium chloride
2-[5-(N-hydroxyethyl-4-pyridinylidene)-3-isopropyl-1-formazano]-1,3-dihydroxyethylbenzimidazolium chloride
2-[5-(N-hydroxyethyl-4-pyridinylidene)-3-(4'-methoxyphenyl)-1-formazano]-1,3-dihydroxyethylbenzimidazolium chloride
2-[5-(N-hydroxyethyl-4-pyridinylidene)-3-(4'-hydroxyphenyl)-1-formazano]-1,3-dihydroxyethylbenzimidazolium chloride
2-[5-(N-hydroxyethyl-4-pyridinylidene)-3-(4'-N,N-dimethylaminophenyl)-1-formazano]-1,3-dihydroxyethylbenzimidazolium chloride
2-[5-(N-carboxyethyl-4-pyridinylidene)-1-formazano]-1,3-dicarboxyethylbenzimidazolium chloride
2-[5-(N-carboxyethyl-4-pyridinylidene)-3-methyl-1-formazano]-1,3-dicarboxyethylbenzimidazolium chloride
2-[5-(N-carboxyethyl-4-pyridinylidene)-3-ethyl-1-formazano]-1,3-dicarboxyethylbenzimidazolium chloride
2-[5-(N-carboxyethyl-4-pyridinylidene)-3-phenyl-1-formazano]-1,3-dicarboxyethylbenzimidazolium chloride
2-[5-(N-carboxyethyl-4-pyridinylidene)-3-isopropyl-1-formazano]-1,3-dicarboxyethylbenzimidazolium chloride
2-[5-(N-carboxyethyl-4-pyridinylidene)-3-(4'-methoxyphenyl)-1-formazano]-1,3-dicarboxyethylbenzimidazolium chloride
2-[5-(N-carboxyethyl-4-pyridinylidene)-3-(4'-hydroxyphenyl)-1-formazano]-1,3-dicarboxyethylbenzimidazolium chloride
2-[5-(N-carboxyethyl-4-pyridinylidene)-3-(4'-N,N-dimethylaminophenyl)-1-formazano]-1,3-dicarboxyethylbenzimidazolium chloride G. Preferably, the compounds of formula (I') are chosen from the family defined by the compounds for which $W'_1$ is a 2-imidazolium radical and $W'_2$ is a 2-pyridine radical. Even more preferably, they are the following compounds:
2-[5-(N-methyl-2-pyridinylidene)-1-formazano]-1,3-dimethylimidazolium chloride
2-[5-(N-methyl-2-pyridinylidene)-3-methyl-1-formazano]-1,3-dimethylimidazolium chloride
2-[5-(N-methyl-2-pyridinylidene)-3-ethyl-1-formazano]-1,3-dimethylimidazolium chloride
2-[5-(N-methyl-2-pyridinylidene)-3-isopropyl-1-formazano]-1,3-dimethylimidazolium chloride
2-[5-(N-methyl-2-pyridinylidene)-3-phenyl-1-formazano]-1,3-dimethylimidazolium chloride
2-[5-(N-methyl-2-pyridinylidene)-3-(4'-methoxyphenyl)-1-formazano]-1,3-dimethylimidazolium chloride
2-[5-(N-methyl-2-pyridinylidene)-3-(4'-hydroxyphenyl)-1-formazano]-1,3-dimethylimidazolium chloride
2-[5-(N-methyl-2-pyridinylidene)-3-(4'-N,N-dimethylaminophenyl)-1-formazano]-1,3-dimethylimidazolium chloride
2-[5-(N-hydroxyethyl-2-pyridinylidene)-1-formazano]-1,3-dihydroxyethylimidazolium chloride
2-[5-(N-hydroxyethyl-2-pyridinylidene)-3-methyl-1-formazano]-1,3-dihydroxyethylimidazolium chloride
2-[5-(N-hydroxyethyl-2-pyridinylidene)-3-ethyl-1-formazano]-1,3-dihydroxyethylimidazolium chloride
2-[5-(N-hydroxyethyl-2-pyridinylidene)-3-phenyl-1-formazano]-1,3-dihydroxyethylimidazolium chloride
2-[5-(N-hydroxyethyl-2-pyridinylidene)-3-isopropyl-1-formazano]-1,3-dihydroxyethylimidazolium chloride
2-[5-(N-hydroxyethyl-2-pyridinylidene)-3-(4'-methoxyphenyl)-1-formazano]-1,3-dihydroxyethylimidazolium chloride
2-[5-(N-hydroxyethyl-2-pyridinylidene)-3-(4'-hydroxyphenyl)-1-formazano]-1,3-dihydroxyethylimidazolium chloride
2-[5-(N-hydroxyethyl-2-pyridinylidene)-3-(4'-N,N-dimethylaminophenyl)-1-formazano]-1,3-dihydroxyethylimidazolium chloride
2-[5-(N-carboxyethyl-2-pyridinylidene)-1-formazano]-1,3-dicarboxyethylimidazolium chloride
2-[5-(N-carboxyethyl-2-pyridinylidene)-3-methyl-1-formazano]-1,3-dicarboxyethylimidazolium chloride
2-[5-(N-carboxyethyl-2-pyridinylidene)-3-ethyl-1-formazano]-1,3-dicarboxyethylimidazolium chloride
2-[5-(N-carboxyethyl-2-pyridinylidene)-3-phenyl-1-formazano]-1,3-dicarboxyethylimidazolium chloride
2-[5-(N-carboxyethyl-2-pyridinylidene)-3-isopropyl-1-formazano]-1,3-dicarboxyethylimidazolium chloride
2-[5-(N-carboxyethyl-2-pyridinylidene)-3-(4'-methoxyphenyl)-1-formazano]-1,3-dicarboxyethylimidazolium chloride
2-[5-(N-carboxyethyl-2-pyridinylidene)-3-(4'-hydroxyphenyl)-1-formazano]-1,3-dicarboxyethylimidazolium chloride
2-[5-(N-carboxyethyl-2-pyridinylidene)-3-(4'-N,N-dimethylaminophenyl)-1-formazano]-1,3-dicarboxyethylimidazolium chloride H. Preferably, the compounds of formula (I') are chosen from the family defined by the compounds for which $W'_1$ is a 2-imidazolium radical and $W'_2$ is a 4-pyridine radical. Even more preferably, they are the following compounds:
2-[5-(N-methyl-4-pyridinylidene)-1-formazano]-1,3-dimethylimidazolium chloride
2-[5-(N-methyl-4-pyridinylidene)-3-methyl-1-formazano]-1,3-dimethylimidazolium chloride
2-[5-(N-methyl-4-pyridinylidene)-3-ethyl-1-formazano]-1,3-dimethylimidazolium chloride
2-[5-(N-methyl-4-pyridinylidene)-3-isopropyl-1-formazano]-1,3-dimethylimidazolium chloride
2-[5-(N-methyl-4-pyridinylidene)-3-phenyl-1-formazano]-1,3-dimethylimidazolium chloride
2-[5-(N-methyl-4-pyridinylidene)-3-(4'-methoxyphenyl)-1-formazano]-1,3-dimethylimidazolium chloride
2-[5-(N-methyl-4-pyridinylidene)-3-(4'-hydroxyphenyl)-1-formazano]-1,3-dimethylimidazolium chloride
2-[5-(N-methyl-4-pyridinylidene)-3-(4'-N,N-dimethylaminophenyl)-1-formazano]-1,3-dimethylimidazolium chloride
2-[5-(N-hydroxyethyl-4-pyridinylidene)-1-formazano]-1,3-dihydroxyethylimidazolium chloride
2-[5-(N-hydroxyethyl-4-pyridinylidene)-3-methyl-1-formazano]-1,3-dihydroxyethylimidazolium chloride
2-[5-(N-hydroxyethyl-4-pyridinylidene)-3-ethyl-1-formazano]-1,3-dihydroxyethylimidazolium chloride
2-[5-(N-hydroxyethyl-4-pyridinylidene)-3-phenyl-1-formazano]-1,3-dihydroxyethylimidazolium chloride
2-[5-(N-hydroxyethyl-4-pyridinylidene)-3-isopropyl-1-formazano]-1,3-dihydroxyethylimidazolium chloride 2-[5-(N-hydroxyethyl-4-pyridinylidene)-3-(4'-methoxyphenyl)-1-formazano]-1,3-dihydroxyethylimidazolium chloride 2-[5-(N-hydroxyethyl-4-pyridinylidene)-3-(4'-hydroxyphenyl)-1-formazano]-1,3-dihydroxyethylimidazolium chloride 2-[5-(N-hydroxyethyl-4-pyridinylidene)-3-(4'-N,N-dimethylaminophenyl)-1-formazano]-1,3-dihydroxyethylimidazolium chloride 2-[5-(N-carboxyethyl-4-pyridinylidene)-1-formazano]-1,3-dicarboxyethylimidazolium chloride 2-[5-(N-carboxyethyl-4-pyridinylidene)-3-methyl-1-formazano]-1,3-dicarboxyethylimidazolium chloride 2-[5-(N-carboxyethyl-4-pyridinylidene)-3-ethyl-1-formazano]-1,3-dicarboxyethylimidazolium chloride 2-[5-(N-carboxyethyl-4-pyridinylidene)-3-phenyl-1-formazano]-1,3-dicarboxyethylimidazolium chloride 2-[5-(N-carboxyethyl-4-pyridinylidene)-3-isopropyl-1-formazano]-1,3-dicarboxyethylimidazolium chloride 2-[5-(N-carboxyethyl-4-pyridinylidene)-3-(4'-methoxyphenyl)-1-formazano]-1,3-dicarboxyethylimidazolium chloride 2-[5-(N-carboxyethyl-4-pyridinylidene)-3-(4'-hydroxyphenyl)-1-formazano]-1,3-dicarboxyethylimidazolium chloride 2-[5-(N-carboxyethyl-4-pyridinylidene)-3-(4'-N,N-dimethylaminophenyl)-1-formazano]-1,3-dicarboxyethylimidazolium chloride The novel compounds and novel families of compounds given in the above lists may be used as direct dyes in the dye compositions according to the invention.

The present invention also relates to a process for preparing the compound of formula (I'), in which at least two equivalents of at least one hydrazone chosen from the hydrazones of formula A and the hydrazones of formula B:

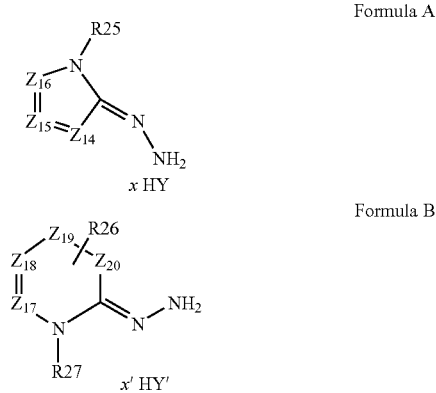

Formula A

Formula B in which $Z_{14}$, $Z_{15}$, $Z_{16}$ and $R_{25}$ have the same meanings as $Z'_7$, $Z'_8$, $Z'_{13}$, and $R'_5$, respectively, of formula (IV)',
Y being an organic or mineral anion,
x being an integer ranging from 1 to 3,
$Z_{17}$, $Z_{18}$, $Z_{19}$, $Z_{20}$, $R_{26}$ and $R_{27}$ have the same meanings as $Z'_9$, $Z'_{10}$, $Z'_{11}$, $Z'_{12}$, $R'_{12}$ and $R'_7$, respectively, of formula (V'),
Y' being an organic or mineral anion,
x' being an integer ranging from 1 to 3, are reacted with one equivalent of an aldehyde of formula $R_{23}CHO$, $R_{23}$ having the same meaning as $R'_0$ of formula (I'). Two equivalents of the same hydrazone or of two different hydrazones may thus be reacted.

According to one preferred variant, the aldehyde of formula $R_{23}CHO$ is generated in the reaction medium from an aldehyde precursor of formula $R'_{23}CH_2OH$ in the presence of an oxidizing system; $R'_{23}$ then has the same meaning as $R'_0$ of formula (I').

This oxidizing system may be a chemical oxidizing agent or a biocatalytic oxidizing agent such as an enzyme.

In particular, the process for preparing the compound of formula (I') according to the present invention, and the process for preparing the compound of formula (I) may be performed in the presence of an aldehyde precursor of formula $R'_{23}CH_2OH$ and of at least one enzyme capable of generating an aldehyde from the aldehyde precursor of formula $R'_{23}CH_2OH$.

The process for enzymatically synthesizing the compounds of formula (I) defined above is performed by reacting at least two equivalents of at least one hydrazone chosen from the hydrazones of formula A and the hydrazones of formula B in which $Z_{14}$, $Z_{15}$, $Z_{16}$ and $R_{25}$ have the same meanings as $Z_7$, $Z_8$, $Z_{13}$ and $R_5$, respectively, of formula (IV),
Y being an organic or mineral anion,
x being an integer ranging from 1 to 3,
$Z_{17}$, $Z_{18}$, $Z_{19}$, $Z_{20}$, $R_{26}$ and $R_{27}$ having the same meanings as $Z_9$, $Z_{10}$, $Z_{11}$, $Z_{12}$, $R_8$ and $R_7$, respectively, of formula (V),
Y' being an organic or mineral anion,
x' being an integer ranging from 1 to 3, with one equivalent of an aldehyde of formula $R_{23}CHO$, $R_{23}$ having the same meaning as $R_0$ of formula (I).

A subject of the present invention is also such a process.

Depending on the reagents used, the reaction is performed with or without an oxidizing system, with or without a cofactor for the enzyme, and with or without a system for regenerating the cofactor.

For the purpose of the present patent application, the term "without an oxidizing system" means that no oxidizing system other than atmospheric oxygen is used.

Preferably, the reaction is performed in aerobic medium at a pH of between 3 and 11 and at a temperature of between 6° C. and 80° C.

More generally, the aldehyde precursor that may be used to prepare the compound of formula (I') or the compound of formula (I) may be chosen from primary alcohols, sarcosine, 4-hydroxymandelate, N6-methyllysine, dimethylglycine, methylglutamate, 2-oxo acids, for example 2-oxo acid pyruvate, benzoylformate, phenylpyruvate or threonine. It will preferably be chosen from primary alcohols.

The enzymes capable of generating an aldehyde from this aldehyde precursor may be chosen especially from the alcohol dehydrogenases EC 1.1.1.1, the alcohol dehydrogenases EC 1.1.1.2, the alcohol dehydrogenases EC 1.1.1.71, the aromatic alcohol dehydrogenases EC 1.1.1.90, also known as aryl alcohol dehydrogenases, the aromatic alcohol dehydrogenases EC 1.1.1.97, the 3-hydroxybenzyl alcohol dehydrogenases EC 1.1.1.97, the coniferyl alcohol dehydrogenases EC 1.1.1.194, the cinnamyl alcohol dehydrogenases EC 1.1.1.195, the methanol dehydrogenases EC 1.1.1.244, the aromatic alcohol oxidases EC 1.1.3.7, also known as aryl alcohol oxidases, the alcohol oxidases EC 1.1.3.13, the 4-hydroxymandelate oxidases EC 1.1.3.19, the long-chain hydrocarbon alcohol oxidases EC 1.1.3.20, the methanol oxidases EC 1.1.3.31, the alcohol dehydrogenases EC 1.1.99.20, the sarcosine oxidases EC 1.5.3.1, the N6-methyllysine oxidases EC 1.5.3.4, the dimethylglycine oxidases EC 1.5.3.10, the sarcosine dehydrogenases EC 1.5.99.1, the dimethylglycine dehydrogenases EC 1.5.99.2, the methylglutamate dehydrogenases EC 1.5.99.5, the 2-oxo acid decarboxylases EC 4.1.1.1, the benzoylformate decarboxylases EC 4.1.1.7, the phenylpyruvate decarboxylases EC 4.1.1.43 and the threonine aldolases EC 4.1.2.5.

Mention may also be made of the following enzymes capable of generating an aldehyde, the preferred substrate of which is given in parentheses: N-methyl L-amino acid oxidase EC 1.5.3.2 (N-methyl-L-amino acid), trimethylamine dehydrogenase EC 1.5.99.7 (trimethylamine), dimethylamine dehydrogenase EC 1.5.99.10 (dimethylamine), nitroethane oxidase EC 1.7.3.1 (nitroethane), indole 2,3-dioxigenase EC 1.13.11.17 (indole), taurine dioxigenase EC 1.14.11.17 (taurine), acetoin ribose 5 phosphate transaldolase EC 2.2.1.4 (3-hydroxybutan-2-one), diamine aminotransferase EC 2.6.1.29 (alpha omega diamine+2-oxogluterate), alkenylglycerophosphocholine hydrolase EC 3.3.2.2 (alkenylglycerophosphocholine), alkenylglycerophosphoethanolamine hydrolase EC 3.3.2.5 (alkenylglycerophosphocholine), alkylalidase EC 3.8.1.1 (halomethane), phosphonoacetaldehyde hydrolase EC 3.11.1.1 (phosphonoacetaldehyde), indolepyruvate decarboxylase EC 4.1.1.74 (3-indol-3-yl pyruvate) mandelonitrile lyase EC 4.1.2.10 (mandelonitrile), hydroxymandelonitrile lyase EC 4.1.2.11 (hydroxymandelonitrile), ketopantoaldolase EC 4.1.2.12 (2-hydroxy-2-isopropylbutanedioate), dimethylaniline-N-oxide aldolase EC 4.1.2.24 (dimethylaniline-N-oxide), phenylserine aldolase EC 4.1.2.26 (phenylserine), sphinganine-1-phosphate aldolase EC 4.1.2.27 (sphinganine-1-phosphate), 17-alpha hydroxyprogesterone aldolase EC 4.1.2.30 (17-alpha hydroxyprogesterone), trimethylamine oxide aldolase EC 4.1.2.23 (trimethylamine oxide), fucosterol epoxide lyase EC 4.1.2.23 (fucosterol epoxide), (3E)-4-(2-carboxyphenyl)-2-oxobut-3-enoate aldolase EC 4.1.2.34 ((3E)-4-(2-carboxyphenyl)-2-oxobut-3-enoate), lactate aldolase EC 4.1.2.36 (lactate), benzoin aldolase EC 4.1.2.38 (benzoin), octoamine dehydratase EC 4.2.1.87 (1-(4-hydroxyphenyl)-2-aminoethanol), synephrine dehydratase EC 4.2.1.88 (1-(4-hydroxyphenyl)-2-(methylamino)ethanol), ethanolamine phosphate phospholyase EC 4.2.3.2 (ethanolamine phosphate), ethanolamine ammonia lyase EC 4.3.1.7 (ethanolamine), dichloromethane dehalogenase EC 4.5.1.3 (dichloromethane), styrene oxide isomerase EC 5.3.99.7 (styrene oxide).

The enzyme capable of generating an aldehyde from the aldehyde precursor used in the dye composition according to the invention may be derived from an extract of plants, of animals, of microorganisms (bacterium, fungus, yeast or microalga) or from viruses, or from cells that are differentiated or undifferentiated, obtained in vivo or in vitro, which are genetically modified or unmodified, or synthetic (obtained via chemical or biotechnological synthesis).

Examples of useful enzymes that may be mentioned in particular are the genera *Plectranthus, Pinus, Gastropode, Manduca, Pichia, Candida, Pleurotus,* and *Pseudomonas,* and even more particularly the following species: *Plectranthus colloides, Pinus strobus,* which is a species of plant origin, *Gastropode mollusc* and *Manduca sexta,* which are of animal origin, *Pichia pastoris* and *Candida boidinii,* which are yeasts, *Pleurotus pulmonarius,* which is a fungus, and *Pseudomonas pseudoalcaligenes,* which is a bacterium.

The choice of the enzyme depends on the nature of the aldehyde precursor. For example, when the aldehyde precursor is an alcohol, then the enzyme is chosen from enzymes capable of generating an aldehyde from this alcohol. When the aldehyde precursor is methylglutamate, then the enzyme is a methylglutamate dehydrogenase.

According to one preferred variant, the aldehyde precursor is a primary alcohol and the enzyme is an enzyme capable of generating the aldehyde from an alcohol. For example, when the primary alcohol is a $C_1$-$C_6$ aliphatic alcohol, then the enzyme capable of generating the aldehyde is chosen from alcohol oxidases, alcohol dehydrogenases, methanol dehydrogenases and methanol oxidases. When the primary alcohol is benzyl alcohol, 4-tert-butylbenzyl alcohol, 3-hydroxy-4-methoxybenzyl alcohol, veratryl alcohol, 4-methoxybenzyl alcohol, cinnamyl alcohol or 2,4-hexadien-1-ol, aryl alcohol oxidases or aromatic alcohol dehydrogenases may be used as aldehyde precursor.

For the enzyme dehydrogenases, it is essential to include the cofactor(s) required for their activity, more specifically $NAD^+$ or $NADP^+$ or other molecules capable of acting as electron acceptor. The addition of a system for regenerating the cofactors may be used for reaction purposes or economic purposes. This regeneration system may be enzymatic, chemical or electrochemical.

A very wide variety of oxidizing agents may be used to perform this process: aqueous hydrogen peroxide solution, organic peracids such as peracetic acid, persalts such as permanganate, perborate and persulfates, chromates or bichromates, hypochlorites, hypobromites, ferricyanides, and peroxides such as manganese dioxide or lead dioxide. Aqueous hydrogen peroxide solution will preferably be used.

The concentration of enzyme substrate (aldehyde precursor) may be between 0.001 M and 6 M and preferably between 0.1 M and 4 M.

The reaction may be performed between pH 3 and pH 11 and preferably between pH 5 and pH 9.5.

The reaction temperature may be between 10° C. and 80° C. and preferably between 20° C. and 65° C.

The hydrazone concentration of the reaction medium is between 0.01 M and 3 M and preferably between 0.1 M and 1M.

The content of cofactor for said enzymes may be between 0.01 mM and 1 M and preferably between 0.1 mM and 10 mM.

During the implementation of the synthesis of the compounds of formulae (I') and (I), the reagents: the hydrazone(s), the enzyme(s), the substrate for said enzyme, and/or the cofactor for said enzyme, and the oxidizing agent and/or the system for regenerating the cofactor are mixed together, and the pH and the temperature are adjusted.

The present invention also relates to a process for preparing the compound of formula (I'), in which a compound of formula (F1) or (F2)

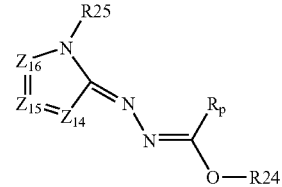

Formula F1

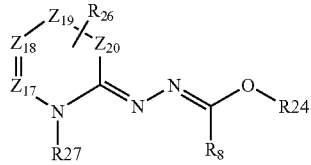

Formula F2 with $Z_{14}$, $Z_{15}$, $Z_{16}$, $R_0$, $R_{24}$ and $R_{25}$ for formula F1 and $Z_{17}$, $Z_{18}$, $Z_{19}$, $Z_{20}$, $R_0$, $R_{24}$ and $R_{26}$ for formula F2 having the meanings described above, is reacted in the presence of one equivalent of a hydrazone of formula (A) or (B).

According to one preferred variant, the compounds of formula (F1) or (F2) may be obtained by reacting a compound of formula $R''_{23}C(OR_{24})_3$ and a hydrazone of formula (A) or (B) in the presence or absence of a protic solvent whose boiling point ranges between 66° C. and 180° C. $R''_{23}$ has the same meaning as $R'_0$ of formula (I') and $R_{24}$ represents a radical chosen from methyl and ethyl groups.

Preferably, the reaction is performed in the presence of triethyl orthoformate and trimethyl orthoacetate at a temperature of between 0° C. and 150° C. for a period of between 30 minutes and 12 hours.

Preferably, the protic solvent is chosen from $H_2O$, ethanol and methanol.

EXAMPLES OF SYNTHESIS

A) Synthetic Process Using at Least One Hydrazone of Formula (A) and/or (B) and an Aldehyde Precursor of Formula $R'_{23}CH_2OH$ The compounds cited in formula (I') may be synthesized by reacting at least one hydrazone as defined in formulae (A) and (B) with one or more enzymes such as: alcohol oxidase, alcohol dehydrogenase, oxidoreductase transferase, and/or lyase, and the substrate(s) of formula $R'_{23}CH_2OH$ for said enzyme(s) with or without oxidizing agent, with or without cofactor for the enzyme, and with or without a system for regenerating said cofactor. The reaction is performed at between pH 3 and pH 11 in aerobic medium at a temperature of between 10° C. and 80° C.

Example 1

| | |
|---|---|
| Ethanol (100%) | 2 M |
| Alcohol oxidase (*Pichia pastoris*) | 1000 U |
| N-hydroxyethylpyridone-2-hydrazone | 0.3 M |
| 30 mM buffer $KH_2PO_4/K_2HPO_4$ pH 7 | qs 100 ml |

Example 2

| | |
|---|---|
| Methanol (100%) | 2.5 M |
| Alcohol oxidase (*Candida boidinii*) | 2000 U |
| 4-methoxy-N-methylpyridone-2-hydrazone | 0.3 M |
| 30 mM buffer $KH_2PO_4/K_2HPO_4$ pH 7 | qs 100 ml |

Example 3

| | |
|---|---|
| Ethanol (100%) | 2 M |
| Extract of *Plectranthus colloides* | 0.4 g |
| 4-methoxy-N-methylpyridone-2-hydrazone | 0.3 M |
| 30 mM buffer $KH_2PO_4/K_2HPO_4$ pH 7 | qs 100 ml |

Example 4

| | |
|---|---|
| Benzyl alcohol (100%) | 1 M |
| Extract of *Pleurotus pulmonarius* | 0.4 g |
| N-hydroxyethylpyridone-2-hydrazone | 0.3 M |
| 30 mM buffer $KH_2PO_4/K_2HPO_4$ pH 9 | qs 100 ml |

Example 5

| | |
|---|---|
| Methanol (100%) | 2.5 M |
| Alcohol dehydrogenase (*Saccharomyces cervisiae*) | 1000 U |
| NAD+ | 10 mM |
| N-methylpyridone-2-hydrazone | 0.3 M |
| 3% aqueous hydrogen peroxide solution | 0.5 ml |
| 30 mM buffer $KH_2PO_4/K_2HPO_4$ pH 9 | qs 100 ml |

Example 6

| | |
|---|---|
| Ethanol (100%) | 2.5 M |
| Alcohol oxidase (*Pichia pastoris*) | 2000 U |
| 1,3-dimethylimidazolidone-2-hydrazone | 0.3 M |
| 30 mM buffer $KH_2PO_4/K_2HPO_4$ pH 8.5 | qs 100 ml |

Example 7

| | |
|---|---|
| Methanol (100%) | 2.5 M |
| Alcohol oxidase (*Pichia pastoris*) | 2000 U |
| 1,3-dimethylimidazolidone-2-hydrazone | 0.3 M |
| 30 mM buffer $KH_2PO_4/K_2HPO_4$ pH 8.5 | qs 100 ml |

Example 8

| | |
|---|---|
| Methanol (100%) | 2.5 M |
| Alcohol oxidase (*Pichia pastoris*) | 2000 U |
| N-methylpyridone-2-hydrazone | 0.3 M |

| | -continued | |
|---|---|---|
| N-hydroxyethylpyridone-2-hydrazone | | 0.3 M |
| 30 mM buffer | | qs 100 ml |
| KH$_2$PO$_4$/K$_2$HPO$_4$ pH 8.5 | | |

Example 9

| | | |
|---|---|---|
| Ethanol | | 1 M |
| Alcohol oxidase (*Pichia pastoris*) | | 50 U |
| (2-methyl-6-methoxy-4H-pyridazin-3-ylidene)hydrazine | | 0.1 M |
| 200 mM buffer | | qs 10 ml |
| KH$_2$PO$_4$/K$_2$HPO$_4$ pH 8.5 | | |

Example 10

| | | |
|---|---|---|
| Ethanol | | 1 M |
| Alcohol oxidase (*Pichia pastoris*) | | 50 U |
| (2-methyl-6-pyrrolidon-1-yl-4H-pyridazin-3-ylidene)hydrazine | | 0.1 M |
| 200 mM buffer | | qs 10 ml |
| KH$_2$PO$_4$/K$_2$HPO$_4$ pH 8.5 | | |

Example 11

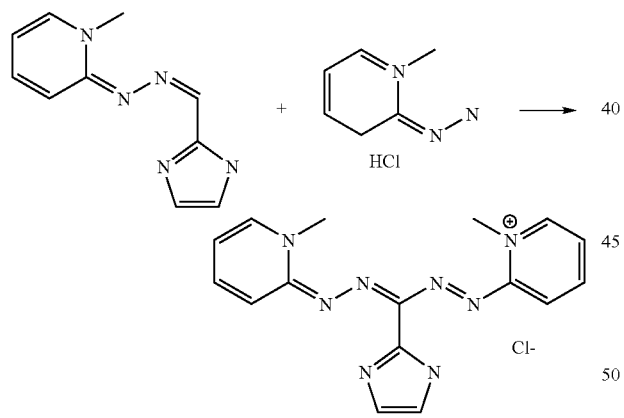

The following reaction was performed:

| | | |
|---|---|---|
| Laccase | | 100 U |
| Alcohol oxidase (*Pichia pastoris*) | | 50 U |
| N-methylpyridone-2-hydrazone | | 0.1 M |
| 200 mM buffer | | qs 10 ml |
| KH$_2$PO$_4$/K$_2$HPO$_4$ pH 8.5 | | |

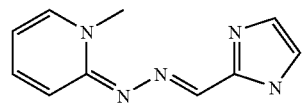 0.1 M

A coloration appeared between 1 minute and 24 hours at room temperature.

| Example | Color | Formula of the isolated product |
|---|---|---|
| 1 | Blue | (structure) |
| 2 | Violet | (structure) |
| 3 | Violet | (structure) |
| 4 | Violet-blue | (structure) |
| 5 | Violet-blue | (structure) |
| 6 | Fuchsia-red | (structure) |
| 7 | Fuchsia-red | (structure) |

-continued

| Example | Color | Formula of the isolated product |
|---|---|---|
| 8 | Dark blue | [structure: pyridinium-N=N-C(H)=N-N=pyridine with N-CH₃ and N-CH₂CH₂OH substituents] |

Example 1

Detection by ESI+M+=329 Lambda Max 578 nm

Example 2

Detection by ESI+M+=315 Lambda Max 556 nm

Example 3

Detection by ESI+M+=329 Lambda Max 564 nm

Example 4

Detection by ESI+M+=391 Lambda Max 576 nm

Example 5

Detection by ESI+M+=255 Lambda Max 569 nm

Example 6

Detection by ESI+M+=275 Lambda Max 528 nm

Example 7

Detection by ESI+M+=261 Lambda Max 534 nm

Example 8

Detection by ESI+M+=285 Lambda Max 572 nm

A coloration appears between 24 hours and 72 hours at room temperature.

| Example | Color | Formula of the isolated product |
|---|---|---|
| 9 | Violet-blue | [structure: bis(methoxy-methylpyridazine) linked by N=N–C(CH₃)=N–N, Cl⁻] |
| 10 | Blue | [structure: bis(pyrrolidinyl-methylpyridazine) linked by N=N–C(CH₃)=N–N, Cl⁻] |
| 11 | Violet-blue | [structure: bis(N-methylpyridine) linked by N=N–C(imidazolyl)=N–N, Cl⁻] |

Example 9

Lambda Max 568 nm

Example 10

Lambda Max 630 nm

Example 11

Lambda Max 556 nm

The products isolated after reaction correspond to the compounds of general formula (I').

B) Synthetic Process Using at Least One Hydrazone of Formula (A) and/or (B) and an Aldehyde of Formula $R_{23}CHO$ This synthetic process is performed in two steps:

1—A hydrazone of formula (A) or (B) is first reacted in the presence of an aldehyde of formula $R_{23}CHO$, at least one polar solvent and an organic salt. A compound of formula (A') or (B') represented below is formed and isolated:

Formula A'

Formula B'

The meanings of the radicals $Z_{14}$, $Z_{15}$, $Z_{16}$, $Z_{17}$, $Z_{18}$, $Z_{19}$, $Z_{20}$, $R_{23}$, $R_{25}$, $R_{26}$ and $R_{27}$ in the compounds of formula (A') or (B') are the same as those in the compounds of formula (A) and (B).

EXAMPLES OF SYNTHESIS OF FORMULAE A' AND B'

Syntheses Performed

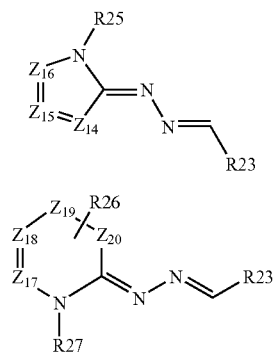

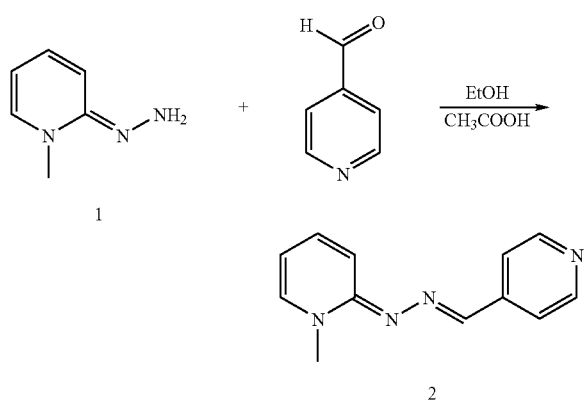

The hydrazone 1 (1 g, 4.6 mmol) was placed in contact with 4-pyridinecarboxaldehyde (0.7 ml, 7 mmol), 0.5 ml of acetic acid and 6 ml of ethanol in a round-bottomed flask with stirring at 45° C. for 30 minutes. After reaction, the reaction medium was concentrated to dryness. The residue was taken up by adding 50 ml of ethyl acetate. The precipitate obtained was filtered off and then dried in a desiccator. 1 g of a yellow powder was obtained.

Analysis:

MS (ES$^+$): 213 (MH$^+$)

NMR ($^1$H, 400 MHz: 4.21 ppm (s, CH$_3$); 7.36 ppm (m, 1H); 8.26 ppm (m, 2H); 8.37 ppm (m, 1H); 8.47 ppm (m, 2H); 8.80 ppm (s, 1H); 8.91 ppm (m, 2H).

The following products were synthesized according to the same procedure:

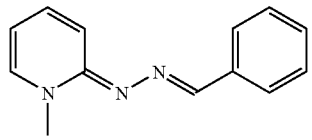

Analysis:

Slightly colored powder

Yield: 98%

MS (ES$^+$): 212 (MH$^+$)

NMR ($^1$H, 400 MHz: 4.1 ppm (s, CH$_3$); 7.16 ppm (m, 1H) 7.49 ppm (m, 2 Har); 7.81 ppm (m, 2 Har); 7.97 ppm (m, 1H); 8.12 ppm (m, 1 Har); 8.35 ppm (m, 1H); 8.97 ppm (s, 1H).

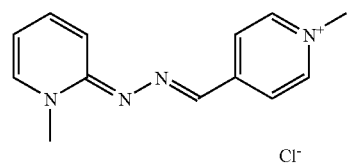

Analysis:

Yellow powder

Yield: quantitative

MS (ES$^+$): 227 (M$^+$)

NMR ($^1$H, 400 MHz: 4.2 ppm (s, CH$_3$); 4.4 ppm (m, 1H); 7.37 ppm (m, 2H); 8.26 ppm (m, 2H); 8.44 ppm (m, 2H); 8.75 ppm (s, 1H); 8.93 ppm (m, 2H).

2—The reaction is performed between pH 3 and pH 11 and preferably between pH 5 and pH 9.5 in aerobic medium at a temperature of between 10° C. and 80° C. and preferably between 20° C. and 65° C. The oxidoreductases used will be chosen from the following enzymes from the group EC 1.10.3, by way of example: catechol oxidase EC 1.10.3.1, laccase EC 1.10.3.2, L-ascorbate oxidase EC 1.10.3.3 and aminophenol oxidase EC 1.10.3.4.

The compound of formula (A') or (B') is the substrate for said enzyme(s). A mediator may be introduced into the reaction mixture in order to improve the reaction speed. Said mediator serves as an intermediate reagent between the enzyme and the compound of formula (A') or (B') or the compound of formula (A) or (B).

As examples of mediators that may be used, mention may be made of 1-hydroxybenzotriazole, ABTS and TEMPO. The concentration of compound of formula (A) or (B) in the reaction medium is between 0.01 M and 3 M and preferably between 0.1 M and 1 M. The concentration of compound of formula (A') or (B') in the reaction medium is between 0.01 M and 3 M and preferably between 0.1 M and 1 M.

The reagents: the compound of formula (A) or (B) and the compound of formula (A') or (B'), the enzyme(s) and/or the mediator for said enzyme, and/or the oxidizing agent are mixed together and the pH and temperature are adjusted.

Example 12

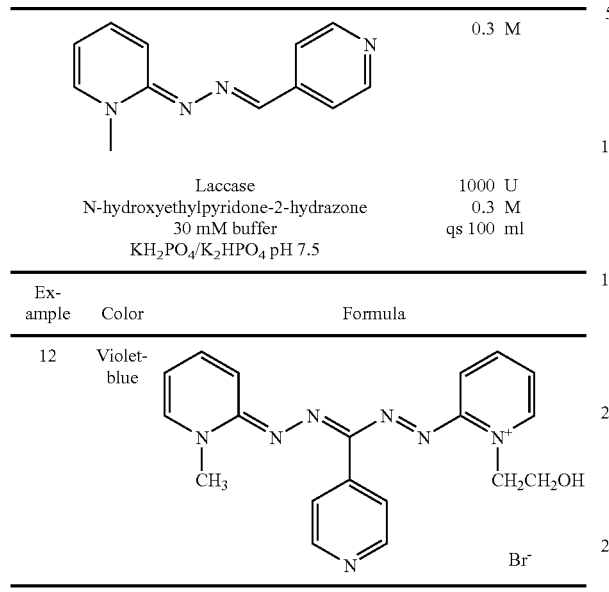

| Example | Color | Formula |
|---------|-------|---------|
| 12 | Violet-blue | 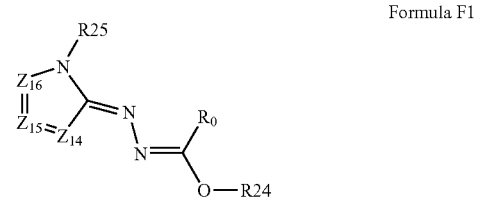 |

C) Synthetic Process Using at Least One Hydrazone of Formula (A) and/or (B) and a Compound of Formula $R''_{23}C(OR_{24})_3$ The hydrazone of formula (A) or (B) used for the synthesis is reacted in the presence of one equivalent of a compound of formula $R''_{23}C(OR_{24})_3$ and optionally a protic solvent with a boiling point ranging between 66° C. and 180° C., at a temperature of between 30° C. and 150° C. with stirring. Preferably, the hydrazone of formula (A) or (B) is reacted in the presence of trimethyl orthoformate or triethyl orthoacetate and optionally a solvent, preferably chosen from methanol and ethanol, at a temperature of between 100° C. and 150° C., for a period of between 30 and 60 minutes.

Depending on the nature of the hydrazone used, a compound of formulae (F1), (F2) or (G1), (G2) below may be obtained:

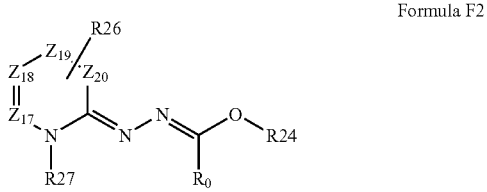

Formula F1

Formula F2

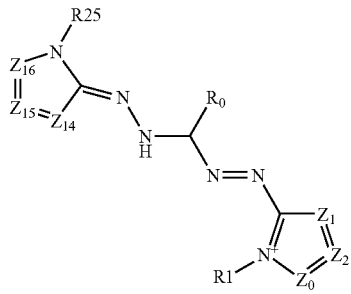

Formula G1

Formula G2

When the compounds of formula (F1) or (F2) are obtained, they may be subsequently converted into tetraazapentamethine compounds of formula (I) in the following manner:

The compound of formula (F1) or (F2) and a compound of formula (A) or (B) are reacted in the presence of an oxidizing agent in a polar solvent, at a temperature of between 0° C. and 120° C. The pH of the solution is between 3 and 11.5. The oxidizing agent is chosen from $O_2$, $Na_2O$, $K_3Fe(CN)_6$, $MnO_2$, $H_2O_2$, $Ag_2O$, $AgO$, $NiO_2$, $NaBO_3$, $Na_2S_2O_8$, $CH_3CO_3H$, $C_6H_5CO_3H$, $(NH_4)_2Ce(NO_3)_6$, $PbO_2$, $Pb(OCOCH_3)_4$, $SeO_2$ and $CrO_3.2C_5H_4N$. The preferred oxidizing agents will be chosen from $K_3Fe(CN)_6$, $MnO_2$, $H_2O_2$ and $Pb(OCOCH_3)_4$. Preferably, the preferred oxidizing agents will be chosen from $O_2$, $K_3Fe(CN)_6$, $MnO_2$ and $H_2O_2$. The reaction is preferably performed at a temperature of between 0° C. and 80° C. in a solvent, preferably a polar solvent, at a pH of between 5 and 9.5.

EXAMPLES OF SYNTHESIS OF FORMULAE G1 AND G2

The hydrazone 1 (0.23 g, 1 mmol) was placed in contact with triethyl orthoformate (0.15 ml, 1 mmol) in a round-bottomed flask with stirring at 130° C. for 30 minutes. After reaction, the reaction medium was concentrated to dryness. The residue was taken up by adding 10 ml of diisopropyl ether. The precipitate obtained was filtered off and then dried in a desiccator. 0.15 g of a white powder was obtained.

Yield: 41%.

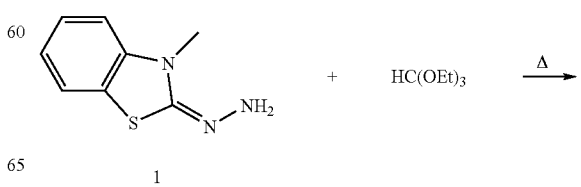

1

-continued

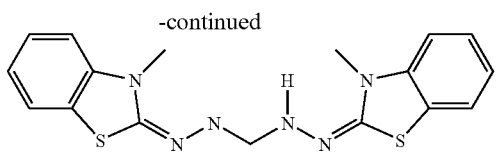
2

Analysis:
White powder
NMR (1H, 400 MHz): 3.63 ppm (s, 2CH₃); 7.2 ppm (m, 2H); 7.30 ppm (m, 2H); 7.43 ppm (m, 2H); 7.59 ppm (m, 2H); 8.17 ppm (s, 1H).

Example 13

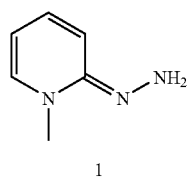
1

HC(OEt)₃ / EtOH Reflux →

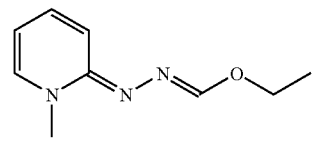
2

1 + 2 →(K₃Fe(CN)₆, NH₄OH)→

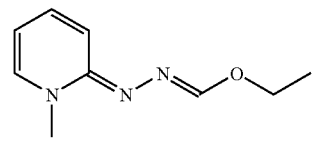

1st Step

The hydrazone 1 (4.28 g, 0.01998 mol) is placed in contact with triethyl orthoformate (50 ml, 0.30 mol) in a round-bottomed flask with stirring at 130° C. for 12 hours. The reaction medium was cooled and the product was precipitated from diisopropyl ether. The precipitate was filtered off under vacuum and then stored under argon. Quantitative yield.

Analysis:
MS (ES⁺): 180 (MH⁺)
NMR (1H, 400 MHz): 1.38 ppm (t, CH₃); 3.93 ppm (m, CH₃) 4.30 ppm (t, CH₂); 6.97 ppm (m, Har); 7.64 ppm (m, Har); 8.15-7.97 ppm (m, 2 Har); 8.36 ppm (s, CH).

2nd Step

Compound 2 (0.1 g, 0.558 mol), compound 1 (0.119 g, 0.558 mol) and pyridine (16.74 ml) were stirred in a round-bottomed flask. The medium was heterogeneous. Aqueous ammonia (0.84 ml, rapid addition) and aqueous potassium hexacyanoferrate (III) solution (K₃Fe(CN)₆/H₂O: 0.81 g/5.94 ml, rapid dropwise addition) were then successively added to the reaction medium. A violet and then dark blue coloration was obtained after stirring for 1.5 hours. The product was precipitated in the presence of diisopropyl ether and ethyl acetate, and then filtered off. It was subsequently washed with ethyl acetate.

Analysis:
MS (ES⁺): 255 (M⁺)
λmax: 589 nm
ε=79800

Example 14

Step 1

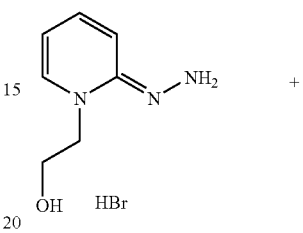
1

+

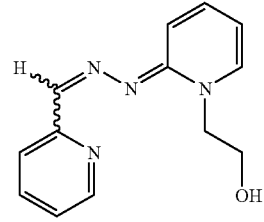
2

O₂, EtOH / 1M NaOH / pH 7, 5-8 / 72 h →

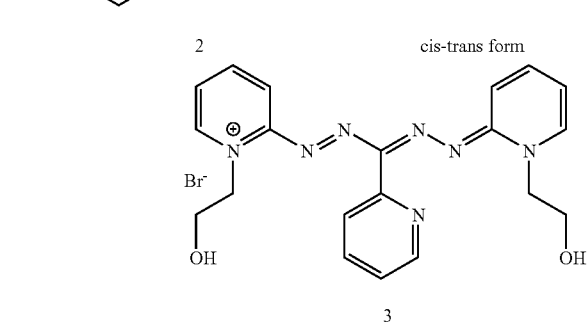
3    cis-trans form 2.42 g of the hydrazone (1) (0.01 mol) and 3.15 g of compound (2) (0.01 mol) in 60 ml of ethanol are stirred in a beaker. 1 M sodium hydroxide solution is added to pH 7.5. The reaction is stirred in the open air for 72 hours. The reaction is monitored by TLC. Once the reaction is complete, 100 ml of acetone are added to the reaction medium, which is stirred for 30 minutes. A dark precipitate appears. This precipitate is filtered off and then dried under vacuum. A dark blue powder is obtained.

Step 2

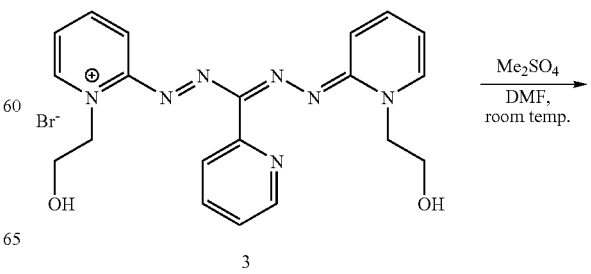
3

Me₂SO₄ / DMF, room temp. →

-continued

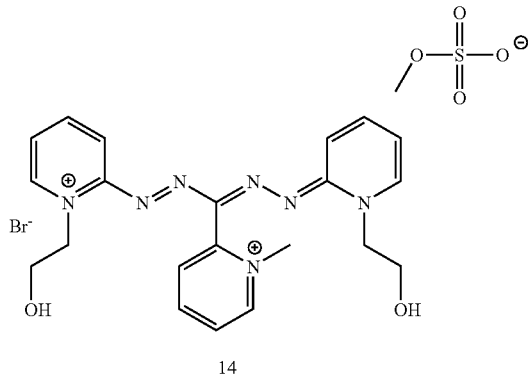

14

0.5 g of compound 3 obtained in the preceding step is dissolved in 3 ml of DMF in a round-bottomed flask. 1 ml of dimethyl sulfate is then added. The reaction is stirred for 15 hours. The reaction medium changed color, changing from blue to fuchsia. The reaction medium is poured into diisopropyl ether. The residue obtained is taken up in ethanol. By successive addition of ethyl acetate and acetone, a precipitate is observed and then filtered off and finally dried in a desiccator. A dark fuchsia powder is obtained.

The synthesis presented above allowed the following compounds to be prepared:

| Example | Color | Formula |
|---------|-------|---------|
| 15 | Blue | |
| 16 | Violet | |

Application Example

The following dye composition was prepared: (amounts expressed as grams of active material)

| | |
|---|---|
| Dye of Example 1 according to the invention | 0.2 |
| Hydroxyethylcellulose | 0.72 |
| Nonionic surfactant: | 3.00 |
| (50/50 C8/C10)alkyl polyglucoside as an aqueous 60% solution | |

-continued

| | |
|---|---|
| Benzyl alcohol | 4.00 |
| Polyethylene glycol (8 EO) | 6.00 |
| Preserving agents | 0.06 |
| Borate buffer qs pH 9 | 50 |
| Demineralized water | 100 |

The composition was applied on the one hand to locks of natural gray hair containing 90% white hairs, and on the other hand to locks of permanent-waved gray hair containing 90% white hairs, for 30 minutes at room temperature (20° C.)

After the leave-in time, the locks were rinsed, shampooed and then rinsed and dried. They were dyed in a very chromatic violet-blue shade.

Example of Bleaching a) Dyeing

An aqueous solution of dye of Example 1 according to the invention (at 0.5% by weight) is applied to a lock of natural gray hair containing 90% white hairs (0.5 g), at pH 7 (0.1 M potassium phosphate buffer) and is left to act on the hair for 30 minutes at room temperature (20° C.).

The lock is then rinsed, shampooed and then dried. It was dyed in a very chromatic violet-blue shade.

b) Bleaching 5 ml of aqueous sodium hydrosulfite (or sodium dithionite) solution at 5% by weight buffered to pH 7 with potassium phosphate (0.1 M) is applied to a 0.5 g lock of hair obtained from step a), and is left to act on the hair for 5 minutes at room temperature (20° C.).

The lock is then rinsed, shampooed and then dried.

The lock obtained is bleached.

A lock of gray hair, i.e. the initial color of the hair before the dyeing treatment (step a), is obtained.

The invention claimed is:

1. A tetraazapentamethine compound of formula (I′):

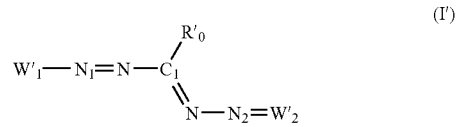

wherein:

W′₁ represents a cationic heteroaromatic radical of formula (II′) or (III′):

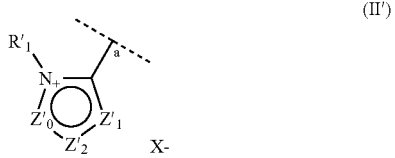

-continued

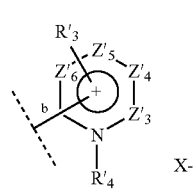
(III')

W'$_2$ represents a heteroaromatic radical of formula (IV') or (V'):

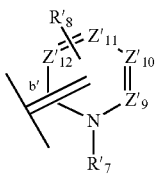
(IV')

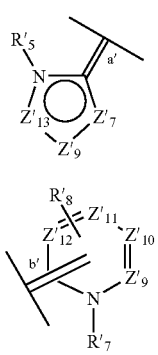
(V')

wherein:
Z'$_0$ represents a radical CR'$_2$, a nitrogen atom or a radical NR'$_{21}$,
Z'$_1$ represents an oxygen atom or a radical NR'$_9$,
Z'$_2$ represents a nitrogen atom or a radical CR'$_{10}$,
Z'$_3$ represents a nitrogen atom or a radical CR'$_{11}$,
Z'$_4$ represents a nitrogen atom or a radical CR'$_{12}$,
Z'$_5$ represents a nitrogen atom or a radical CR'$_{13}$,
Z'$_6$ represents a nitrogen atom or a radical CR'$_{14}$,
Z'$_7$ represents an oxygen atom, or a radical NR'$_{15}$,
Z'$_8$ represents a nitrogen atom or a radical CR'$_{16}$,
Z'$_9$ represents a nitrogen atom or a radical CR'$_{17}$,
Z'$_{10}$ represents a nitrogen atom or a radical CR'$_{18}$,
Z'$_{11}$ represents a nitrogen atom or a radical CR'$_{19}$,
Z'$_{12}$ represents a nitrogen atom or a radical CR'$_{20}$,
Z'$_{13}$ represents a radical CR'$_6$, a nitrogen atom or a radical NR'$_{22}$,
wherein each of the rings of formulae (II'), (III'), (IV') and (V') comprise not more than three nitrogen atoms and two of the three nitrogen atoms may be contiguous,
the bond a of the 5-membered cationic heteroaromatic radical of formula (II') being linked to the nitrogen atom N$_1$ of formula (I'),
the bond b of the 6-membered cationic heteroaromatic radical of formula (III') being linked to the nitrogen atom N$_1$ of formula (I'),
the double bond a' of the 5-membered heteroaromatic radical of formula (IV') being linked to the nitrogen atom N$_2$ of formula (I'),
the double bond b' of the 6-membered heteroaromatic radical of formula (V') being linked to the nitrogen atom N$_2$ of formula (I'),
the bond b, linking the cationic heteroaromatic radical of formula (III') to the nitrogen atom N$_1$ of formula (I'), being in an ortho or para position relative to the nitrogen atom bearing the radical R'$_4$ when Z'$_5$ represents a radical CR'$_{13}$; the bond b being in an ortho position relative to the nitrogen atom bearing the radical R'$_4$ when Z'$_5$ represents a nitrogen atom,
the bond b', linking the heteroaromatic radical of formula (V') to the nitrogen atom N$_2$ of formula (I'), being in an ortho or para position relative to the nitrogen atom bearing the radical R'$_7$ when Z'$_{11}$ represents a radical CR'$_{19}$; the bond b' being in an ortho position relative to the nitrogen atom bearing the radical R'$_7$ when Z'$_{11}$ represents a nitrogen atom,
R'$_2$, R'$_6$, R'$_{10}$ and R'$_{16}$ represent, independently of each other, a hydrogen atom; a linear or branched C$_1$-C$_4$ alkyl radical, which is unsubstituted or substituted with one to three radicals chosen from hydroxyl, C$_1$-C$_2$ alkoxy, C$_2$-C$_4$ (poly)-hydroxyalkoxy, amino, C$_1$-C$_2$ (di)alkylamino, carboxyl and sulfonic radicals; a phenyl radical, which is unsubstituted or substituted with one or two radicals chosen from hydroxyl, C$_1$-C$_2$ alkoxy, C$_2$-C$_4$ (poly)-hydroxyalkoxy, amino and C$_1$-C$_2$ (di)alkylamino; a carboxyl radical; a sulfonylamino radical,
R'$_1$, R'$_4$, R'$_5$, R'$_7$, R'$_9$, R'$_{15}$ and R'$_{22}$ represent, independently of each other, a linear or branched C$_1$-C$_8$ alkyl radical, which is unsubstituted or substituted with one to three radicals chosen from hydroxyl, C$_1$-C$_2$ alkoxy, C$_2$-C$_4$ (poly)-hydroxyalkoxy, amino, C$_1$-C$_2$ (di)alkylamino, carboxyl and sulfonic radicals;
R'$_0$, R'$_3$, R'$_8$, R'$_{11}$, R'$_{12}$, R'$_{13}$, R'$_{14}$, R'$_{17}$, R'$_{18}$, R'$_{19}$ and R'$_{20}$ represent, independently of each other, a hydrogen atom, a linear or branched C$_1$-C$_{16}$ hydrocarbon-based chain, this chain possibly being saturated or unsaturated with one to three unsaturations, this chain being unsubstituted or substituted with one to three radicals chosen from hydroxyl, C$_1$-C$_2$ alkoxy, C$_2$-C$_4$ (poly)-hydroxyalkoxy, amino, C$_1$-C$_2$ (di)alkylamino, carboxyl, sulfonic, sulfonylamino and C$_2$-C$_4$ (poly)-hydroxyalkylamino radicals or a halogen atom; a phenyl radical, which is unsubstituted or substituted with one to three radicals chosen from hydroxyl, C$_1$-C$_2$ alkoxy, C$_2$-C$_4$ (poly)-hydroxyalkoxy, amino, C$_1$-C$_2$ (di)alkylamino, carboxyl, sulfonic, sulfonylamino and C$_2$-C$_4$ (poly)-hydroxyalkylamino radicals or a halogen atom; a heteroaryl radical chosen from pyrazolyl, pyrrolyl, imidazolyl, thiazolyl, oxazolyl, triazolyl, pyridyl, pyrimidinyl, triazinyl, pyrazinyl and pyridazinyl radicals; in addition, this hydrocarbon-based chain may be interrupted with one or two oxygen, nitrogen, sulphur atoms or with an SO$_2$ radical,
R'$_2$ with R'$_{10}$, R'$_{11}$ with R'$_{12}$, R'$_6$ with R'$_{16}$, and R'$_{17}$ with R'$_{18}$, being able to form independently of each other, a 5- or 6-membered carbon-based aromatic ring, which is unsubstituted or substituted with one or two hydroxyl, amino, (di)(C$_1$-C$_2$)alkylamino, C$_1$-C$_2$ alkoxy or C$_2$-C$_4$ (poly)hydroxyalkylamino radicals, subject to W'$_1$ and W'$_2$ not representing, simultaneously, the same bicyclic system,
wherein R'$_0$, R'$_3$, R'$_8$, R'$_{11}$, R'$_{12}$, R'$_{14}$, R'$_{17}$, R'$_{18}$, R'$_{19}$ and R'$_{20}$ do not comprise a peroxide bond, or diazo or nitroso radicals,
X is an organic or inorganic anion.
2. The compound of formula (I') as claimed in claim 1, wherein R'$_0$ represents a hydrogen atom; a linear or branched C$_1$-C$_6$ alkyl radical, which is unsubstituted or substituted with one to three radicals chosen from hydroxyl, C$_1$-C$_2$ alkoxy, C$_2$-C$_4$ (poly)-hydroxyalkoxy, amino, C$_1$-C$_2$ (di)alkylamino, C$_2$-C$_4$ (poly)hydroxyalkylamino, carboxyl and sulfonic radicals; a phenyl radical, which is unsubstituted or substituted with one to three radicals chosen from hydroxyl, C$_1$-C$_2$ alkoxy, $C_2$-$C_4$ (poly)-hydroxyalkoxy, amino, $C_1$-$C_2$ (di)alkylamino, carboxyl and sulfonic radicals or a halogen atom; an optionally cationic heteroaryl radical chosen from pyrazolyl, pyrrolyl, imidazolyl, thiazolyl, oxazolyl, triazolyl, pyridyl, pyrimidinyl, triazinyl, pyrazinyl and pyridazinyl radicals.

3. The compound of formula (I') as claimed in claim 1, wherein $R'_0$ represents a hydrogen atom; a methyl, ethyl or 2-methoxyethyl radical; a phenyl radical, which is unsubstituted or substituted with an amino, (di)methylamino or (di)(2-hydroxyethyl) radical, or optionally a cationic heteroaryl radical chosen from pyrazolyl, pyrrolyl, imidazolyl and pyridyl radicals.

4. The compound of formula (I') as claimed in claim 1, wherein $R'_2$, $R'_6$, $R'_{10}$ and $R'_{16}$ represent a hydrogen atom, a $C_1$-$C_4$ alkyl radical, which is unsubstituted or substituted with one or two radicals chosen from hydroxyl, amino, $C_1$-$C_2$ (di)alkylamino and carboxyl radicals, or a phenyl radical.

5. The compound of formula (I') as claimed in claim 1, wherein $R'_2$, $R'_6$, $R'_{10}$ and $R'_{16}$ represent a hydrogen atom, a methyl, phenyl, 2-hydroxymethyl radical, or a carboxy.

6. The compound of formula (I') as claimed in claim 1, wherein $R'_1$, $R'_4$, $R'_5$, $R'_7$, $R'_9$, $R'_{15}$, $R'_{21}$ and $R'_{22}$ represent a $C_1$-$C_4$ alkyl radical, which is unsubstituted or substituted with one or two radicals chosen from hydroxyl, $C_1$-$C_2$ alkoxy, amino, $C_1$-$C_2$ (di)alkylamino, carboxyl and sulfonic radicals.

7. The compound of formula (I') as claimed in claim 1, wherein $R'_1$, $R'_4$, $R'_5$, $R'_7$, $R'_9$, $R'_{15}$, $R'_{21}$ and $R'_{22}$ represent a methyl, ethyl, 2-hydroxyethyl, 1-carboxymethyl, 2-carboxyethyl or 2-sulfonylethyl radical.

8. The compound of formula (I') as claimed in claim 1, wherein $R'_3$, $R'_8$, $R'_{11}$, $R'_{12}$, $R'_{13}$, $R'_{14}$, $R'_{17}$, $R'_{18}$, $R'_{19}$ and $R'_{20}$ represent, independently of each other, a hydrogen atom; a linear or branched $C_1$-$C_4$, alkyl radical, which is unsubstituted or substituted with one or two radicals chosen from hydroxyl, $C_1$-$C_2$ alkoxy, $C_2$-$C_4$ (poly)-hydroxyalkoxy, amino, $C_1$-$C_2$ (di)alkylamino, carboxyl and sulfonic radicals; a phenyl radical, which is unsubstituted or substituted with one or two radicals chosen from hydroxyl, $C_1$-$C_2$ alkoxy, $C_2$-$C_4$ (poly)-hydroxyalkoxy, amino, $C_1$-$C_2$ (di)alkylamino, carboxyl and sulfonic radicals or a halogen atom; a sulfonylamino radical; a $C_2$-$C_4$ (poly)-hydroxyalkylamino radical.

9. The compound of formula (I') as claimed in claim 1, wherein $R'_3$, $R'_8$, $R'_{11}$, $R'_{12}$, $R'_{13}$, $R'_{14}$, $R'_{17}$, $R'_{18}$, $R'_{19}$ and $R'_{20}$ represent, independently of each other, a hydrogen atom, a methyl or 2-hydroxymethyl radical, a carboxyl, a methoxy, ethoxy or 2-hydroxyethyloxy radical, or an amino, methylamino, dimethylamino or 2-hydroxyethylamino radical.

10. The compound of formula (I') as claimed in claim 1, wherein $W'_1$ is a 2-pyridinium radical and $W'_2$ is a 2-pyridine radical, selected from the group consisting of:

2-[5-(N-methyl-2-pyridinylidene)-1-formazano]-N-methylpyridinium chloride

2-[5-(N-methyl-2-pyridinylidene)-3-methyl-1-formazano]-N-methylpyridinium chloride 2-[5-(N-methyl-2-pyridinylidene)-3-ethyl-1-formazano]-N-methylpyridinium chloride 2-[5-(N-methyl-2-pyridinylidene)-3-isopropyl-1-formazano]-N-methylpyridinium chloride 2-[5-(N-methyl-2-pyridinylidene)-3-phenyl-1-formazano]-N-methylpyridinium chloride 2-[5-(N-methyl-2-pyridinylidene)-3-(4'-methoxyphenyl)-1-formazano]-N-methylpyridinium chloride 2-[5-(N-methyl-2-pyridinylidene)-3-(4'-hydroxyphenyl)-1-formazano]-N-methylpyridinium chloride 2-[5-(N-methyl-2-pyridinylidene)-3-(4'-N,N-dimethylaminophenyl)-1-formazano]-N-methylpyridinium chloride 2-[5-(4-pyrrolidino-N-methyl-2-pyridinylidene)-1-formazano]-4-pyrrolidino-N-methylpyridinium chloride 2-[5-(4-pyrrolidino-N-methyl-2-pyridinylidene)-3-methyl-1-formazano]-4-pyrrolidino-N-methylpyridinium chloride 2-[5-(4-pyrrolidino-N-methyl-2-pyridinylidene)-3-ethyl-1-formazano]-4-pyrrolidino-N-methylpyridinium chloride 2-[5-(4-pyrrolidino-N-methyl-2-pyridinylidene)-3-isopropyl-1-formazano]-4-pyrrolidino-N-methylpyridinium chloride 2-[5-(4-pyrrolidino-N-methyl-2-pyridinylidene)-3-phenyl-1-formazano]-4-pyrrolidino-N-methylpyridinium chloride 2-[5-(4-pyrrolidino-N-methyl-2-pyridinylidene)-3-(4'-methoxyphenyl)-1-formazano]-4-pyrrolidino-N-methylpyridinium chloride 2-[5-(4-pyrrolidino-N-methyl-2-pyridinylidene)-3-4'-hydroxyphenyl)-1-formazano]-4-pyrrolidino-N-methylpyridinium chloride 2-[5-(4-pyrrolidino-N-methyl-2-pyridinylidene)-3-(4'-N,N-dimethylaminophenyl)-1-formazano]-4-pyrrolidino-N-methylpyridinium chloride 2-[5-(N-hydroxyethyl-2-pyridinylidene)-1-formazano]-N-hydroxyethylpyridinium chloride 2-[5-(N-hydroxyethyl-2-pyridinylidene)-3-methyl-1-formazano]-N-hydroxyethyl-pyridinium chloride 2-[5-(N-hydroxyethyl-2-pyridinylidene)-3-ethyl-1-formazano]-N-hydroxyethyl-pyridinium chloride 2-[5-(N-hydroxyethyl-2-pyridinylidene)-3-phenyl-1-formazano]-N-hydroxyethyl-pyridinium chloride 2-[5-(N-hydroxyethyl-2-pyridinylidene)-3-isopropyl-1-formazano]-N-hydroxyethyl-pyridinium chloride 2-[5-(N-hydroxyethyl-2-pyridinylidene)-3-(4'-methoxyphenyl)-1-formazano]-N-hydroxyethyl-pyridinium chloride 2-[5-(N-hydroxyethyl-2-pyridinylidene)-3-(4'-hydroxyphenyl)-1-formazano]-N-hydroxyethyl-pyridinium chloride 2-[5-(N-hydroxyethyl-2-pyridinylidene)-3-(4'-N,N-dimethylaminophenyl)-1-formazano]-N-hydroxyethyl-pyridinium chloride 2-[5-(N-carboxyethyl-2-pyridinylidene)-1-formazano]-N-carboxyethyl-pyridinium chloride 2-[5-(N-carboxyethyl-2-pyridinylidene)-3-methyl-1formazano]-N-carboxyethyl-pyridinium chloride 2-[5-(N-carboxyethyl-2-pyridinylidene)-3-ethyl-1formazano]-N-carboxyethyl-pyridinium chloride 2-[5-(N-carboxyethyl-2-pyridinylidene)-3-phenyl-1formazano]-N-carboxyethyl-pyridinium chloride 2-[5-(N-carboxyethyl-2-pyridinylidene)-3-isopropyl-1formazano]-N-carboxyethyl-pyridinium chloride 2-[5-(N-carboxyethyl-2-pyridinylidene)-3-(4'-methoxyphenyl)-1 formazano]-N-carboxyethyl-pyridinium chloride 2-[5-(N-carboxyethyl-2-pyridinylidene)-3-(4'-hydroxyphenyl)-1 formazano]-N-carboxyethyl-pyridinium chloride and 2-[5-(N-carboxyethyl-2-pyridinylidene)-3-(4'-N,N-dimethylaminophenyl)-1 formazano]-N-carboxyethyl-pyridinium chloride.

11. A compound of formula (I') as claimed in claim 1, wherein $W'_1$ is a 4-pyridinium radical and $W'_2$ is a 4-pyridine radical, selected from the group consisting of:

4-[5-(N-methyl-4-pyridinylidene)-1-formazano]-N-methylpyridinium chloride

4-[5-(N-methyl-4-pyridinylidene)-3-methyl-1-formazano]-N-methylpyridinium chloride 4-[5-(N-methyl-4-pyridinylidene)-3-ethyl-1-formazano]-N-methylpyridinium chloride 4-[5-(N-methyl-4-pyridinylidene)-3-isopropyl-1-formazano]-N-methylpyridinium chloride 4-[5-(N-methyl-4-pyridinylidene)-3-phenyl-1-formazano]-N-methylpyridinium chloride 4-[5-(N-methyl-4-pyridinylidene)-3-(4'-methoxyphenyl)-1-formazano]-N-methylpyridinium chloride 4-[5-(N-methyl-4-pyridinylidene)-3-(4'-hydroxyphenyl)-1-formazano]-N-methylpyridinium chloride 4-[5-(N-methyl-4-pyridinylidene)-3-(4'-N,N-dimethylaminophenyl)-1-formazano]-N-methylpyridinium chloride 4-[5-(N-hydroxyethyl-4-pyridinylidene)-1-formazano]-N-hydroxyethylpyridinium chloride 4-[5-(N-hydroxyethyl-4-pyridinylidene)-3-methyl-1-formazano]-N-hydroxyethylpyridinium chloride 4-[5-(N-hydroxyethyl-4-pyridinylidene)-3-ethyl-1-formazano]-N-hydroxyethylpyridinium chloride 4-[5-(N-hydroxyethyl-4-pyridinylidene)-3-phenyl-1-formazano]-N-hydroxyethylpyridinium chloride 4-[5-(N-hydroxyethyl-4-pyridinylidene)-3-isopropyl-1-formazano]-N-hydroxyethyl pyridinium chloride 4-[5-(N-hydroxyethyl-4-pyridinylidene)-3-(4'-methoxyphenyl)-1-formazano]-N-hydroxyethyl pyridinium chloride 4-[5-(N-hydroxyethyl-4-pyridinylidene)-3-(4'-hydroxyphenyl)-1-formazano]-N-hydroxyethyl-pyridinium chloride 4-[5-(N-hydroxyethyl-4-pyridinylidene)-3-(4'-N,N-dimethylaminophenyl)-1-formazano]-N-hydroxyethyl pyridinium chloride 4-[5-(N-carboxyethyl-4-pyridinylidene)-1-formazano]-N-carboxyethyl-pyridinium chloride 4-[5-(N-carboxyethyl-4-pyridinylidene)-3-methyl-1-formazano]-N-carboxyethyl pyridinium chloride 4-[5-(N-carboxyethyl-4-pyridinylidene)-3-ethyl-1-formazano]-N-carboxyethyl pyridinium chloride 4-[5-(N-carboxyethyl-4-pyridinylidene)-3-phenyl-1-formazano]-N-carboxyethyl pyridinium chloride 4-[5-(N-carboxyethyl-4-pyridinylidene)-3-isopropyl-1-formazano]-N-carboxyethyl pyridinium chloride 4-[5-(N-carboxyethyl-4-pyridinylidene)-3-(4'-methoxyphenyl)-1-formazano]-N-carboxyethyl pyridinium chloride 4-[5-(N-carboxyethyl-4-pyridinylidene)-3-(4'-hydroxyphenyl)-1-formazano]-N-carboxyethyl-pyridinium chloride and 4-[5-(N-carboxyethyl-4-pyridinylidene)-3-(4'-N,N-dimethylaminophenyl)-1-formazano]-N-carboxyethyl pyridinium chloride.

12. The compound of formula (I') as claimed in claim 1, wherein W'$_1$ is a 2-imidazolium radical and W'$_2$ is a 2-imidazole radical, selected from the group consisting of:

2-[5-(1,3-dimethyl-2-imidazolidene)-1-formazano]-1,3-dimethylimidazolium chloride 2-[5-(1,3-dimethyl-2-imidazolidene)-3-methyl-1-formazano]-1,3-dimethyl imidazolium chloride 2-[5-(1,3-dimethyl-2-imidazolidene)-3-ethyl-1-formazano]-1,3-dimethyl imidazolium chloride 2-[5-(1,3-dimethyl-2-imidazolidene)-3-isopropyl-1-formazano]-1,3-dimethyl imidazolium chloride 2-[5-(1,3-dimethyl-2-imidazolidene)-3-phenyl-1-formazano]-1,3-dimethyl imidazolium chloride 2-[5-(1,3-dimethyl-2-imidazolidene)-3-(4'-methoxyphenyl)-1-formazano]-1,3-dimethyl imidazolium chloride 2-[5-(1,3-dimethyl-2-imidazolidene)-3-(4'-hydroxyphenyl)-1-formazano]-1,3-dimethyl imidazolium chloride 2-[5-(1,3-dimethyl-2-imidazolidene)-3-(4'-N,N-dimethylaminophenyl)-1-formazano]-1,3-dimethyl imidazolium chloride 2-[5-(1,3-dihydroxyethyl-2-imidazolidene)-1-formazano]-1,3-dihydroxyethyl-imidazolium chloride 2-[5-(1,3-dihydroxyethyl-2-imidazolidene)-3-methyl-1-formazano]-1,3-dihydroxyethylimidazolium chloride 2-[5-(1,3-dihydroxyethyl-2-imidazolidene)-3-ethyl-1-formazano]-1,3-dihydroxyethyl-imidazolium chloride 2-[5-(1,3-dihydroxyethyl-2-imidazolidene)-3-phenyl-1-formazano]-1,3-dihydroxyethyl-imidazolium chloride 2-[5-(1,3-dihydroxyethyl-2-imidazolidene)-3-isopropyl-1-formazano]-1,3-dihydroxyethyl-imidazolium chloride 2-[5-(1,3-dihydroxyethyl-2-imidazolidene)-3-(4'-methoxyphenyl)-1-formazano]-1,3-dihydroxyethyl-imidazolium chloride 2-[5-(1,3-dihydroxyethyl-2-imidazolidene)-3-(4'-hydroxyphenyl)-1-formazano]-1,3-dihydroxyethyl-imidazolium chloride 2-[5-(1,3-dihydroxyethyl-2-imidazolidene)-3-(4'-N,N-dimethylaminophenyl)-1-formazano]-1,3-dihydroxyethyl-imidazolium chloride 2-[5-(1,3-dicarboxyethyl-2-imidazolidene)-1-formazano]-1,3-dicarboxyethyl-imidazolium chloride 2-[5-(1,3-dicarboxyethyl-2-imidazolidene)-3-methyl-1-formazano]-1,3-dicarboxyethyl-imidazolium chloride 2-[5-(1,3-dicarboxyethyl-2-imidazolidene)-3-ethyl-1-formazano]-1,3-dicarboxyethyl-imidazolium chloride 2-[5-(1,3-dicarboxyethyl-2-imidazolidene)-3-phenyl-1-formazano]-1,3-dicarboxyethyl-imidazolium chloride 2-[5-(1,3-dicarboxyethyl-2-imidazolidene)-3-isopropyl-1-formazano]-1,3-dicarboxyethyl-imidazolium chloride 2-[5-(1,3-dicarboxyethyl-2-imidazolidene)-3-(4'-methoxyphenyl)-1-formazano]-1,3-dicarboxyethyl-imidazolium chloride 2-[5-(1,3-dicarboxyethyl-2-imidazolidene)-3-(4'-hydroxyphenyl)-1-formazano]-1,3-dicarboxyethyl-imidazolium chloride and 2-[5-(1,3-dicarboxyethyl-2-imidazolidene)-3-(4'-N,N-dimethylaminophenyl)-1-formazano]-1,3-dicarboxyethyl-imidazolium chloride.

13. A Composition for dyeing keratin fibers comprising, in a medium that is suitable for dyeing, at least one compound selected from the group consisting of:

2-[5-(N-methyl-2-pyridinylidene)-1-formazano]-N-methylpyridinium chloride

2-[5-(N-methyl-2-pyridinylidene)-3-methyl-1-formazano]-N-methylpyridinium chloride 2-[5-(N-methyl-2-pyridinylidene)-3-ethyl-1-formazano]-N-methylpyridinium chloride 2-[5-(N-methyl-2-pyridinylidene)-3-isopropyl-1-formazano]-N-methylpyridinium chloride 2-[5-(N-methyl-2-pyridinylidene)-3-phenyl-1-formazano]-N-methylpyridinium chloride 2-[5-(N-methyl-2-pyridinylidene)-3-(4'-methoxyphenyl)-1-formazano]-N-methylpyridinium chloride 2-[5-(N-methyl-2-pyridinylidene)-3-(4'-hydroxyphenyl)-1-formazano]-N-methylpyridinium chloride 2-[5-(N-methyl-2-pyridinylidene)-3-(4'-N,N-dimethylaminophenyl)-1-formazano]-N-methylpyridinium chloride 2-[5-(4-pyrrolidino-N-methyl-2-pyridinylidene)-1-formazano]-4-pyrrolidino-N-methylpyridinium chloride
2-[5-(4-pyrrolidino-N-methyl-2-pyridinylidene)-3-methyl-1-formazano]-4-pyrrolidino-N-methylpyridinium chloride
2-[5-(4-pyrrolidino-N-methyl-2-pyridinylidene)-3-ethyl-1-formazano]-4-pyrrolidino-N-methylpyridinium chloride
2-[5-(4-pyrrolidino-N-methyl-2-pyridinylidene)-3-isopropyl-1-formazano]-4-pyrrolidino-N-methylpyridinium chloride
2-[5-(4-pyrrolidino-N-methyl-2-pyridinylidene)-3-phenyl-1-formazano]-4-pyrrolidino-N-methylpyridinium chloride
2-[5-(4-pyrrolidino-N-methyl-2-pyridinylidene)-3-(4'-methoxyphenyl)-1-formazano]-4-pyrrolidino-N-methylpyridinium chloride
2-[5-(4-pyrrolidino-N-methyl-2-pyridinylidene)-3-(4'-hydroxyphenyl)-1-formazano]-4-pyrrolidino-N-methylpyridinium chloride
2-[5-(4-pyrrolidino-N-methyl-2-pyridinylidene)-3-(4'-N,N-dimethylaminophenyl)-1-formazano]-4-pyrrolidino-N-methylpyridinium chloride
2-[5-(N-hydroxyethyl-2-pyridinylidene)-1-formazano]-N-hydroxyethylpyridinium chloride
2-[5-(N-hydroxyethyl-2-pyridinylidene)-3-methyl-1-formazano]-N-hydroxyethyl-pyridinium chloride
2-[5-(N-hydroxyethyl-2-pyridinylidene)-3-ethyl-1-formazano]-N-hydroxyethyl-pyridinium chloride
2-[5-(N-hydroxyethyl-2-pyridinylidene)-3-phenyl-1-formazano]-N-hydroxyethyl-pyridinium chloride
2-[5-(N-hydroxyethyl-2-pyridinylidene)-3-isopropyl-1-formazano]-N-hydroxyethyl-pyridinium chloride
2-[5-(N-hydroxyethyl-2-pyridinylidene)-3-(4'-methoxyphenyl)-1-formazano]-N-hydroxyethyl-pyridinium chloride
2-[5-(N-hydroxyethyl-2-pyridinylidene)-3-(4'-hydroxyphenyl)-1-formazano]-N-hydroxyethyl-pyridinium chloride
2-[5-(N-hydroxyethyl-2-pyridinylidene)-3-(4'-N,N-dimethylaminophenyl)-1-formazano]-N-hydroxyethyl-pyridinium chloride
2-[5-(N-carboxyethyl-2-pyridinylidene)-1-formazano]-N-carboxyethyl-pyridinium chloride
2-[5-(N-carboxyethyl-2-pyridinylidene)-3-methyl-1-formazano]-N-carboxyethyl-pyridinium chloride
2-[5-(N-carboxyethyl-2-pyridinylidene)-3-ethyl-1-formazano]-N-carboxyethyl-pyridinium chloride
2-[5-(N-carboxyethyl-2-pyridinylidene)-3-phenyl-1-formazano]-N-carboxyethyl-pyridinium chloride
2-[5-(N-carboxyethyl-2-pyridinylidene)-3-isopropyl-1-formazano]-N-carboxyethyl-pyridinium chloride
2-[5-(N-carboxyethyl-2-pyridinylidene)-3-(4'-methoxyphenyl)-1-formazano]-N-carboxyethyl-pyridinium chloride
2-[5-(N-carboxyethyl-2-pyridinylidene)-3-(4'-hydroxyphenyl)-1-formazano]-N-carboxyethyl-pyridinium chloride
2-[5-(N-carboxyethyl-2-pyridinylidene)-3-(4'-N,N-dimethylaminophenyl)-1-formazano]-N-carboxyethyl-pyridinium chloride
4-[5-(N-methyl-4-pyridinylidene)-1-formazano]-N-methylpyridinium chloride
4-[5-(N-methyl-4-pyridinylidene)-3-methyl-1-formazano]-N-methylpyridinium chloride
4-[5-(N-methyl-4-pyridinylidene)-3-ethyl-1-formazano]-N-methylpyridinium chloride
4-[5-(N-methyl-4-pyridinylidene)-3-isopropyl-1-formazano]-N-methylpyridinium chloride
4-[5-(N-methyl-4-pyridinylidene)-3-phenyl-1-formazano]-N-methylpyridinium chloride
4-[5-(N-methyl-4-pyridinylidene)-3-(4'-methoxyphenyl)-1-formazano]-N-methylpyridinium chloride
4-[5-(N-methyl-4-pyridinylidene)-3-(4'-hydroxyphenyl)-1-formazano]-N-methylpyridinium chloride
4-[5-(N-methyl-4-pyridinylidene)-3-(4'-N,N-dimethylaminophenyl)-1-formazano]-N-methylpyridinium chloride
4-[5-(N-hydroxyethyl-4-pyridinylidene)-1-formazano]-N-hydroxyethylpyridinium chloride
4-[5-(N-hydroxyethyl-4-pyridinylidene)-3-methyl-1-formazano]-N-hydroxyethylpyridinium chloride
4-[5-(N-hydroxyethyl-4-pyridinylidene)-3-ethyl-1-formazano]-N-hydroxyethylpyridinium chloride
4-[5-(N-hydroxyethyl-4-pyridinylidene)-3-phenyl-1-formazano]-N-hydroxyethylpyridinium chloride
4-[5-(N-hydroxyethyl-4-pyridinylidene)-3-isopropyl-1-formazano]-N-hydroxyethyl pyridinium chloride
4-[5-(N-hydroxyethyl-4-pyridinylidene)-3-(4'-methoxyphenyl)-1-formazano]-N-hydroxyethyl pyridinium chloride
4-[5-(N-hydroxyethyl-4-pyridinylidene)-3-(4'-hydroxyphenyl)-1-formazano]-N-hydroxyethyl-pyridinium chloride
4-[5-(N-hydroxyethyl-4-pyridinylidene)-3-(4'-N,N-dimethylaminophenyl)-1-formazano]-N-hydroxyethyl pyridinium chloride
4-[5-(N-carboxyethyl-4-pyridinylidene)-1-formazano]-N carboxyethyl-pyridinium chloride
4-[5-(N-carboxyethyl-4-pyridinylidene)-3-methyl-1-formazano]-N-carboxyethyl pyridinium chloride
4-[5-(N-carboxyethyl-4-pyridinylidene)-3-ethyl-1-formazano]-N-carboxyethyl pyridinium chloride
4-[5-(N-carboxyethyl-4-pyridinylidene)-3-phenyl-1-formazano]-N-carboxyethyl pyridinium chloride
4-[5-(N-carboxyethyl-4-pyridinylidene)-3-isopropyl-1-formazano]-N-carboxyethyl pyridinium chloride
4-[5-(N-carboxyethyl-4-pyridinylidene)-3-(4'-methoxyphenyl)-1-formazano]-N-carboxyethyl pyridinium chloride
4-[5-(N-carboxyethyl-4-pyridinylidene)-3-(4'-hydroxyphenyl)-1-formazano]-N-carboxyethyl-pyridinium chloride
4-[5-(N-carboxyethyl-4-pyridinylidene)-3-(4'-N,N-dimethylaminophenyl)-1-formazano]-N-carboxyethyl pyridinium chloride
2-[5-(1,3-dimethyl-2-imidazolidene)-1-formazano]-1,3-dimethylimidazolium chloride
2-[5-(1,3-dimethyl-2-imidazolidene)-3-methyl-1-formazano]-1,3-dimethyl imidazolium chloride
2-[5-(1,3-dimethyl-2-imidazolidene)-3-ethyl-1-formazano]-1,3-dimethyl imidazolium chloride
2-[5-(1,3-dimethyl-2-imidazolidene)-3-isopropyl-1-formazano]-1,3-dimethyl imidazolium chloride
2-[5-(1,3-dimethyl-2-imidazolidene)-3-phenyl-1-formazano]-1,3-dimethyl imidazolium chloride
2-[5-(1,3-dimethyl-2-imidazolidene)-3-(4'-methoxyphenyl)-1-formazano]-1,3-dimethyl imidazolium chloride
2-[5-(1,3-dimethyl-2-imidazolidene)-3-(4'-hydroxyphenyl)-1-formazano]-1,3-dimethyl imidazolium chloride
2-[5-(1,3-dimethyl-2-imidazolidene)-3-(4'-N,N-dimethylaminophenyl)-1-formazano]-1,3-dimethyl imidazolium chloride 2-[5-(1,3-dihydroxyethyl-2-imidazolidene)-1-formazano]-1,3-dihydroxyethyl-imidazolium chloride
2-[5-(1,3-dihydroxyethyl-2-imidazolidene)-3-methyl-1-formazano]-1,3-dihydroxyethylimidazolium chloride
2-[5-(1,3-dihydroxyethyl-2-imidazolidene)-3-ethyl-1-formazano]-1,3-dihydroxyethyl-imidazolium chloride
2-[5-(1,3-dihydroxyethyl-2-imidazolidene)-3-phenyl-1-formazano]-1,3-dihydroxyethyl-imidazolium chloride
2-[5-(1,3-dihydroxyethyl-2-imidazolidene)-3-isopropyl-1-formazano]-1,3-dihydroxyethyl-imidazolium chloride
2-[5-(1,3-dihydroxyethyl-2-imidazolidene)-3-(4'-methoxyphenyl)-1-formazano]-1,3-dihydroxyethyl-imidazolium chloride
2-[5-(1,3-dihydroxyethyl-2-imidazolidene)-3-(4'-hydroxyphenyl)-1-formazano]-1,3-dihydroxyethyl-imidazolium chloride
2-[5-(1,3-dihydroxyethyl-2-imidazolidene)-3-(4'-N,N-dimethylaminophenyl)-1-formazano]-1,3-dihydroxyethyl-imidazolium chloride
2-[5-(1,3-dicarboxyethyl-2-imidazolidene)-1-formazano]-1,3-dicarboxyethyl-imidazolium chloride
2-[5-(1,3-dicarboxyethyl-2-imidazolidene)-3-methyl-1-formazano]-1,3-dicarboxyethyl-imidazolium chloride
2-[5-(1,3-dicarboxyethyl-2-imidazolidene)-3-ethyl-1-formazano]-1,3-dicarboxyethyl-imidazolium chloride
2-[5-(1,3-dicarboxyethyl-2-imidazolidene)-3-phenyl-1-formazano]-1,3-dicarboxyethyl-imidazolium chloride
2-[5-(1,3-dicarboxyethyl-2-imidazolidene)-3-isopropyl-1-formazano]-1,3-dicarboxyethyl-imidazolium chloride
2-[5-(1,3-dicarboxyethyl-2-imidazolidene)-3-(4'-methoxyphenyl)-1-formazano]-1,3-dicarboxyethyl-imidazolium chloride
2-[5-(1,3-dicarboxyethyl-2-imidazolidene)-3-(4'-hydroxyphenyl)-1-formazano]-1,3-dicarboxyethyl-imidazolium chloride and
2-[5-(1,3-dicarboxyethyl-2-imidazolidene)-3-(4'-N,N-dimethylaminophenyl)-1-formazano]-1,3-dicarboxyethyl-imidazolium chloride.

14. The composition as claimed in claim 13, wherein the at least one compound is present in a concentration ranging from 0.001% to 5% by weight relative to the total weight of the composition.

15. The composition as claimed in claim 13, wherein said composition further comprises at least one oxidation base selected from the group consisting of para-phenylenediamines, bis(phenyl)alkylenediamines, para-aminophenols, ortho-aminophenols and heterocyclic bases, the addition salts thereof, and mixtures thereof.

16. The composition as claimed in claim 13, wherein said composition further comprises at least one coupler selected from the group consisting of meta-phenylenediamines, meta-aminophenols, meta-diphenols, naphthalene-based couplers and heterocyclic couplers, the addition salts thereof, and mixtures thereof.

17. The composition as claimed in claim 13, wherein said composition further comprises at least one direct dye other than the compounds as recited in claim 13.

18. The composition as claimed in claim 13, wherein said composition further comprises an oxidizing agent.

19. A process for dyeing keratin fibers, wherein at least one composition as claimed in claim 13 is applied to said fibers, for a time that is sufficient to develop the desired coloration.

20. The process as claimed in claim 19, wherein the dye composition further comprises an oxidizing agent.

21. The process as claimed in claim 20, wherein the oxidizing agent is mixed at the time of use with the dye composition.

22. The process as claimed in claim 20, wherein the oxidizing agent is applied to the fibers simultaneously with or sequentially to the dye composition.

23. The process as claimed in claim 19, wherein the dye composition further comprises at least one oxidation base and optionally at least one coupler, in the presence of an oxidizing agent.

24. A process for bleaching dyed keratin fibers, comprising:
a) applying a bleaching composition comprising, in a suitable medium, at least one reducing agent chosen from sulfur-containing reducing agents to said fibers dyed with a dye composition as defined in claim 13,
b) leaving said composition to act for a time that is sufficient to obtain bleaching,
c) optionally rinsing the fibers, and
d) washing, rinsing and drying the fibers.

25. The process as claimed in claim 24, wherein the sulfur-containing reducing agents are selected from the compounds having a thiol, sulfide or sulfite function.

26. The process as claimed in claim 25, wherein the thiols are selected from the group consisting of thioglycolic acid, thiolactic acid, the alkali metal or alkaline-earth metal salts thereof and esters thereof; [beta]-mercaptoethanol; cystein, cysteamine and derivatives thereof; homocystein and a salt thereof; mercaptoaldehydes; penicillamine; glutathione; and mixtures thereof.

27. The process as claimed in claim 25, wherein the sulfites are selected from the group consisting of alkali metal, alkaline-earth metal or ammonium sulfates, metabisulfites or hydrosulfites, and mixtures thereof.

28. A process for preparing the compound of formula (I') as claimed in claim 1, wherein at least two equivalents of at least one hydrazone chosen from the hydrazones of formula A and the hydrazones of formula B:

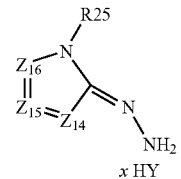

Formula A

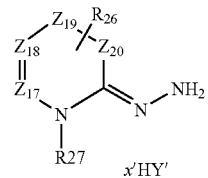

Formula B wherein $Z_{14}$, $Z_{15}$, $Z_{16}$ and $R_{25}$ have the same meanings as $Z'_7$, $Z'_8$, $Z'_{13}$, and $R'_5$, respectively, of formula (IV'),
  Y being an organic or mineral anion,
  x being an integer ranging from 1 to 3,
  $Z_{17}$, $Z_{18}$, $Z_{19}$, $Z_{20}$, $R_{26}$ and $R_{27}$, have the same meanings as $Z'_9$, $Z'_{10}$, $Z'_{11}$, $Z'_{12}$, $R'_8$ and $R'_7$, respectively, of formula (V'),
  Y' being an organic or mineral anion, and
  x' being an integer ranging from 1 to 3, are reacted with one equivalent of an aldehyde of formula $R_{23}CHO$, wherein $R_{23}$ has the same meaning as $R'_0$ of formula (I').

29. The preparation process as claimed in claim 28, wherein the aldehyde of formula $R_{23}CHO$ is obtained from an aldehyde precursor of formula $R'_{23}CH_2OH$ in the presence of an oxidizing system, wherein $R'_{23}$ has the same meaning as $R'_0$ of formula (I') defined in claim 1.

* * * * *